United States Patent
Hauch et al.

(10) Patent No.: US 11,840,734 B2
(45) Date of Patent: Dec. 12, 2023

(54) METHOD FOR ANALYZING AURKA EXPRESSION

(71) Applicant: Qiagen GmbH, Hilden (DE)

(72) Inventors: Siegfried Hauch, Hilden (DE); Markus Sprenger-Haussels, Hilden (DE)

(73) Assignee: Qiagen GmbH, Hilden (DE)

( * ) Notice: Subject to any disclaimer, the term of this patent is extended or adjusted under 35 U.S.C. 154(b) by 0 days.

(21) Appl. No.: 16/494,949

(22) PCT Filed: Mar. 1, 2018

(86) PCT No.: PCT/EP2018/055016
§ 371 (c)(1),
(2) Date: Sep. 17, 2019

(87) PCT Pub. No.: WO2018/184768
PCT Pub. Date: Oct. 11, 2018

(65) Prior Publication Data
US 2020/0010906 A1    Jan. 9, 2020

(30) Foreign Application Priority Data

Apr. 3, 2017 (EP) .................................. 17164667
Apr. 4, 2017 (EP) .................................. 17164820

(51) Int. Cl.
*C12Q 1/6886* (2018.01)
(52) U.S. Cl.
CPC ..... *C12Q 1/6886* (2013.01); *C12Q 2600/106* (2013.01); *C12Q 2600/158* (2013.01)
(58) Field of Classification Search
None
See application file for complete search history.

(56) References Cited

U.S. PATENT DOCUMENTS

| | | | |
|---|---|---|---|
| 2013/0224214 A1* | 8/2013 | Sahin | C07K 16/40 424/174.1 |
| 2014/0315844 A1* | 10/2014 | Kwok | C12Q 1/6886 514/648 |
| 2016/0146819 A1* | 5/2016 | Ince | A61K 31/593 435/6.12 |
| 2016/0264973 A1* | 9/2016 | Aceto | C12Q 1/6886 |

FOREIGN PATENT DOCUMENTS

WO    WO 2016057832    *    4/2016

OTHER PUBLICATIONS

Keup et al. In: Proceedings of the American Association for Cancer Research Annual Meeting 2017; Apr. 1, 2017. Abstract 3777. Available via URL: <//cancerres.aacrjournals.org/content/77/13_Supplement/3777>. (Year: 2017).*
Keup et al. Poster presentation #3777. RNA profiles of circulating tumor cells and extracellular vesicles for therapy stratification of metastatic breast cancer patients. Proceedings of the American Association for Cancer Research Annual Meeting 2017; Apr. 1, 2017 (Year: 2017).*
Bredemeier et al. Oncotarget. May 20, 2016. 7(27): 41677-41690) (Year: 2016).*
International Search Report dated May 25, 2018 filed in PCT/EP2018/055016.
M.R. Speicher et al., "Tumor signatures in the blood," Nature Biotechnology, May 2014, p. 441-443, vol. 32 No. 5, Nature Publishing Group, United Kingdom; Cited in International Search Report.
M. Nagata et al., "Molecular Biomarkers in Bladder Cancer: Novel Potential Indicators of Prognosis and Treatment Outcomes," Disease Markers, Jan. 2016, p. 1-5, vol. 2016, Hindawi Publishing Corporation, United Kingdom; Cited in ISR.
S. Batth et al., "Circulating tumor markers: harmonizing the yin and yang of CTCs and ctDNA for precision medicine," Annals of Oncology, 2017, pp. 468-477, vol. 28 issue 3, Oxford University Press, United Kingdom; Cited in ISR.

* cited by examiner

*Primary Examiner* — Carla J Myers
(74) *Attorney, Agent, or Firm* — Rankin, Hill & Clark LLP

(57) ABSTRACT

Provided is a method for analysing the expression of one or more biomarker RNA molecules, comprising (A) isolating RNA from circulating tumor cells obtained from a subject, determining the expression of at least one biomarker RNA molecule in the isolated RNA and providing an expression profile based on the results; (B) isolating RNA from extracellular vesicles obtained from the subject, determining the expression of at least one biomarker RNA molecule in the isolated RNA and providing an expression profile based on the results; and (C) using the expression profiles determined in (A) and determined in (B) for a combined analysis of the results. Such combined analysis of the CTC and EV expression profiles enhances the prognostic and predictive value of the obtained results and can provide valuable diagnostic, prognostic and/or predictive information. The present method can thus be used as improved diagnostic, prognostic and/or predictive aid in the management of cancer patients. It can be used to support the diagnosis, prognosis or to choose the most appropriate treatment for cancer patients.

9 Claims, 9 Drawing Sheets

Fig. 5 - Table 1 (continues onto additional pages)

| | Marker | Full name |
|---|---|---|
| Basal like 1/2 | EGFR | epidermal growth factor receptor |
| | cMET | MET proto-oncogene, receptor tyrosine kinase |
| | PI3KCA/PI3K | phosphatidylinositol-4,5-bisphosphate 3-kinase catalytic subunit alpha/ phosphatidylinositol-4,5-bisphosphate 3-kinase |
| | PARP | poly(ADP-ribose) polymerase 1 |
| | AURKA | Aurora kinase A |
| | BRAF | v-Raf murine sarcoma viral oncogene homolog B |
| | CK5 | cytokeratin 5 |
| | CK6 | cytokeratin 6 |
| | ERB | estrogen receptor beta |
| | ERK | extracellular signal-regulated kinase |
| | KRAS | Kirsten rat sarcoma viral oncogene homolog |
| | MAPK | mitogen-activated protein kinase |
| | MEK | MAPK/ERK Kinase |
| | P53 | tumor protein p53 |
| | AURKB | Aurora kinase B |
| | BUB1 | budding uninhibited by benzimidazoles 1 |
| | CCNA2 | cyclin A2 |
| | CENPA | centromere protein A |
| | CENPF | centromere protein F |
| | CHEK1 | checkpoint kinase 1 |
| | CK14 | cytokeratin 14 |
| | EPHA2 | ephrin type-A receptor 2 |
| | EXO1 | exonuclease 1 |
| | FANCA | Fanconi anemia complementation group A |
| | FANCG | Fanconi anemia complementation group G |
| | Ki-67 | marker of proliferation Ki-67 |
| | MCM10 | minichromosome maintenance 10 replication initiation factor |
| | MDC1 | mediator of DNA damage checkpoint 1 |
| | MME | membrane metalloendopeptidase |
| | MSH2 | mutS homolog 2 |
| | MYC | v-myc avian myelocytomatosis viral oncogene homolog |
| | NBN | nibrin |
| | NRAS | Neuroblastoma rat sarcoma viral oncogene homolog |
| | PLK1 | polo like kinase 1 |
| | PRC1 | protein regulator of cytokinesis 1 |
| | RAD21 | RAD21 cohesin complex component |
| | RAD51 | RAD51 recombinase |
| | RAD54B | RAD54 homolog B |
| | Survivin | - |
| | TP63 | tumor protein p63 |
| | TTK | TTK protein kinase |

Fig. 5 - Table 1 (continued from previous page)

|  | Marker | Full name |
|---|---|---|
| Epithelial like | KRT5 | keratin 5 |
|  | AFP | α-fetoprotein |
|  | CEA | Carcinoembryonic antigen |
|  | EpCam | epithelial cell adhesion molecule |
|  | KRT 8 | keratin 8 |
|  | KRT 18 | keratin 18 |
|  | KRT 19 | keratin 19 |
|  | KRT 21 | KRT21=KRT20=keratin 20 |
|  | Muc1 | mucin 1, cell surface associated |
|  | Muc16 | mucin 16, cell surface associated |
|  | Muc4 | mucin 4, cell surface associated |
|  | PSA | Prostate-specific antigen |
|  | PSMA | prostate-specific membrane antigen |
| Epithelial to mesenchymal transition/ tumor stem cell | Notch | - |
|  | Akt2 | v-akt murine thymoma viral oncogene homolog 2 |
|  | PI3KCA | phosphatidylinositol-4,5-bisphosphate 3-kinase catalytic subunit alpha |
|  | mTor | mechanistic target of rapamycin |
|  | Her2/3 | human epidermal growth factor receptor 2/3 |
|  | ALK | Anaplastic lymphoma kinase |
|  | ALDH1 | Aldehyde dehydrogenase |
|  | BMI1 | B lymphoma Mo-MLV insertion region 1 homolog |
|  | CD44 | cluster of differentiation 44 |
|  | e-cadherin | - |
|  | Jagged-1 | - |
|  | mesothelin | - |
|  | n-cadherin | - |
|  | Slug | - |
|  | Snail | - |
|  | Twist | twist family bHLH transcription factor 1 |
|  | Vimentin | - |
|  | ABCA8 | ATP binding cassette subfamily A member 8 |
|  | ABCB1 | ATP binding cassette subfamily B member 1 |
|  | ACTA2 | Alpha-actin-2 |
|  | ALDH1 | aldehyde dehydrogenase 1 |
|  | BCL2 | B-cell lymphoma 2 |
|  | BGN | biglycan |
|  | BMP2 | bone morphogenetic protein 2 |
|  | CAV1 | caveolin 1 |
|  | CAV2 | caveolin 2 |
|  | CCND2 | cyclin D2 |
|  | COL3A1 | collagen type III alpha 1 chain |
|  | COL5A2 | collagen type V alpha 2 chain |
|  | CTNNB1 | catenin beta 1 |
|  | DKK2 | dickkopf WNT signaling pathway inhibitor 2 |
|  | DKK3 | dickkopf WNT signaling pathway inhibitor 3 |
|  | ENG | endoglin |
|  | FBN1 | fibrillin 1 |

Fig. 5 - Table 1 (continued from previous page)

| | Marker | Full name |
|---|---|---|
| Epithelial to mesenchymal transition/ tumor stem cell | FZD4 | frizzled class receptor 4 |
| | GNG11 | G protein subunit gamma 11 |
| | HIF1 | hypoxia-inducible factor-1 |
| | HIF2 | hypoxia-inducible factor-2 |
| | HOXA10 | homeobox A10 |
| | HOXA5 | homeobox A5 |
| | ITGAV | integrin subunit alpha V |
| | LDH | lactate dehydrogenase |
| | MEIS1 | Meis homeobox 1 |
| | MEIS2 | Meis homeobox 2 |
| | MEOX1 | mesenchyme homeobox 1 |
| | MEOX2 | mesenchyme homeobox 2 |
| | MMP2 | matrix metallopeptidase 2 |
| | MSX1 | msh homeobox 1 |
| | NGFR | nerve growth factor receptor |
| | NT5E | 5'-nucleotidase ecto |
| | PAI-1 | plasminogen activator inhibitor type-1 |
| | PDGFR | platelet derived growth factor receptor |
| | PER1 | period circadian clock 1 |
| | PROCR | protein C receptor |
| | SERPINE1 | serpin family E member 1 |
| | SFRP4 | secreted frizzled related protein 4 |
| | SMAD6 | SMAD family member 6 |
| | SMAD7 | SMAD family member 7 |
| | SNAI2 | snail family transcriptional repressor 2 |
| | SPARC | secreted protein acidic and cysteine rich |
| | TAGLN | transgelin |
| | TCF4 | transcription factor 4 |
| | TERF2IP | Telomeric repeat-binding factor 2-interacting protein |
| | TGFbeta | transforming growth factor beta |
| | TGFBR | transforming growth factor beta receptor |
| | THY1 | Thy-1 cell surface antigen |
| | TIE1 | tyrosine kinase with immunoglobulin like and EGF like domains 1 |
| | uPA | urokinase plasminogen activator |
| | VCAM1 | vascular cell adhesion molecule 1 |
| | VEGFR | vascular endothelial growth factor receptor |
| | ZEB1 | zinc finger E-box binding homeobox 1 |
| | ZEB2 | zinc finger E-box binding homeobox 2 |

Fig. 5 - Table 1 (continued from previous page)

| | Marker | Full name |
|---|---|---|
| Receptor tyrosine kinase | cKit | KIT proto-oncogene receptor tyrosine kinase |
| | cMET | MET proto-oncogene, receptor tyrosine kinase |
| | EGFR | epidermal growth factor receptor |
| | Her2 | human epidermal growth factor receptor 2 |
| | Her3 | human epidermal growth factor receptor 3 |
| | Her4 | human epidermal growth factor receptor 4 |
| | IGFR | insulin like growth factor receptor |
| | PDGFR | platelet derived growth factor receptor |
| | VEGFR | vascular endothelial growth factor receptor |
| | TEK | TEK receptor tyrosine kinase |
| | TIE1 | tyrosine kinase with immunoglobulin like and EGF like domains 1 |
| Immune modulation | BRCA1 | breast cancer 1 |
| | BRCA2 | breast cancer 2 |
| | CD19 | cluster of differentiation 19 |
| | CD4 | cluster of differentiation 4 |
| | CD45 | cluster of differentiation 45 |
| | CD8 | cluster of differentiation 8 |
| | IFN alpha | interferon alpha |
| | IFN gamma | interferon gamma |
| | PD-1 | programmed cell death 1 |
| | PD-L1 | Programmed death-ligand 1 |
| | TNFbeta | tumor necrosis factor beta |
| | IRF8 | interferon regulatory factor 8 |
| | IRF1 | interferon regulatory factor 1 |
| | IRF7 | interferon regulatory factor 7 |
| | ITK | IL2 inducible T-cell kinase |
| | JAK1 | Janus kinase 1 |
| | JAK2 | Janus kinase 2 |
| | LCK | LCK proto-oncogene, Src family tyrosine kinase |
| | LYN | LYN proto-oncogene, Src family tyrosine kinase |
| | NFKB1 | nuclear factor kappa B subunit 1 |
| | NFKBIA | nuclear factor kappa B inhibitor alpha |
| | NFKBIE | nuclear factor kappa B inhibitor epsilon |
| | RELB | RELB proto-oncogene, NF-kB subunit |
| | STAT1 | signal transducer and activator of transcription 1 |
| | STAT4 | signal transducer and activator of transcription 4 |
| | STAT5A | signal transducer and activator of transcription 5A |
| | BTK | Bruton tyrosine kinase |
| | ZAP70 | zeta chain of T-cell receptor associated protein kinase 70 |

Fig. 5 - Table 1 (continued from previous page)

| | Marker | Full name |
|---|---|---|
| Resistance marker | AURKA | Aurora kinase A |
| | ERCC1 | ERCC excision repair 1; excision repair cross-complementation group 1 |
| | ALDH1 | Aldehyde dehydrogenase |
| | Caspase(all) | cysteine aspartases |
| | CXCR4 | C-X-C chemokine receptor type 4 |
| | Cyclin-D1 | - |
| | Cyclooxygenase2 | - |
| | DPD | dihydropyrimidine dehydrogenase |
| | H2AX | H2A histone family member X |
| | Heregulin | - |
| | Ki-67 | marker of proliferation Ki-67 |
| | MDR1 | multidrug resistance protein 1 |
| | pTEN | phosphatase and tensin homolog |
| | RANK/RANKL | Receptor Activator of Nuclear Factor κ B/RANK-ligand |
| | Survivin | - |
| | Tubulinbeta | - |
| | TYMS | thymidylate synthetase |
| Steroid receptor pathway | AR | androgen receptor |
| | SRC | sarcoma |
| | ARV7 or other AR splice variants | androgen receptor variant 7 |
| | ER | estrogen receptor (vint ER1) |
| | PR | progesterone receptor |
| | ALCAM | activated leukocyte cell adhesion molecule |
| | APOD | apolipoprotein D |
| | CLDN8 | claudin 8 |
| | DHCR24 | 24-dehydrocholesterol reductase |
| | FASN | fatty acid synthase |
| | FKBP5 | FK506 binding protein 5 |
| | PIP | prolactin induced protein |
| | SPDEF | SAM pointed domain containing ETS transcription factor |
| Other | CA 125 | cancer antigen 125 |
| | CA 15-3 | cancer antigen 15-3 |
| | CA 19-9 | cancer antigen 19-9 |
| | CA 72-4 | cancer antigen 72-4 |
| | hCG | human chorionic gonadotropin |

METHOD FOR ANALYZING AURKA EXPRESSION

FIELD OF INVENTION

The present invention provides a method for analyzing the expression of one or more marker molecules. The present method is particularly suitable for use in the field of medical prognosis and diagnosis and can be used to support therapy stratification.

BACKGROUND OF THE INVENTION

Solid cancers are known to shed biological materials into the systemic circulation. These include cells (circulating tumor cells, also referred to as CTCs) and extracellular vesicles (also referred to as EVs) such as exosomes and other types of sub-cellular membrane vesicles. Free circulating nucleic acids are also known to contain cancer-related information, e.g. on mutations.

These biological materials exist in easily accessible bodily fluids, such as peripheral whole blood, peritoneal or pleural effusions, and carry molecular information, including proteins, nucleic acids and lipids. The molecular information provided by these circulating biological materials can be correlated to for example prognosis, therapy response, relapse or therapy resistance mechanisms. There is a high interest in the prior art towards these circulating biological materials for minimally invasive testing. They present significant advantages to circumvent challenges of biopsies and can be easily and repeatedly obtained to provide a minimally invasive reflection of tumor molecular information. It is accepted in the art that free circulating nucleic acids, extracellular vesicles or circulating tumor cells can provide valuable diagnostic, prognostic, predictive and monitoring information. This information can be used e.g. by analyzing biomarkers comprised therein. A biomarker is a biological molecule that is measurable in the biological sample to be analyzed, and which either alone or in combination with other biomarkers can be an indicator of some clinically significant condition. Biomarkers can be e.g. diagnostic, surrogate, prognostic and/or predictive. A biomarker may be a nucleic acid (e.g. a DNA or RNA molecule), a protein, a lipid, a carbohydrate or metabolite.

Despite the well-recognized clinical potential, their use remains challenging. Existing methods that are based on the analysis of molecular biomarkers comprised in free circulating nucleic acids, extracellular vesicles or circulating tumor cells for obtaining cancer-related information often have drawbacks with respect to sensitivity and/or robustness. In particular, improved methods for analyzing molecular biomarkers are needed to help diagnosis, prognosis or to choose the most appropriate treatment for cancer patients.

It is an object of the present invention to overcome at least one drawback of the prior art. It is moreover an object of the present invention to provide an improved method which provides a high sensitivity and robustness in the analysis of circulating molecular information, in particular of molecular biomarkers. It is moreover the object of the present invention to provide an improved method for the analysis of molecular biomarkers as diagnostic, prognostic and/or predictive aid in the management of cancer patients. It is moreover an object to provide improved methods that enable earlier diagnosis of cancer and/or a reliable prediction of therapy resistance or responsiveness to increase the likelihood of successful treatment.

SUMMARY OF THE INVENTION

According to a first aspect, a method for analyzing the expression of one or more biomarker RNA molecules is provided, comprising
  (A) isolating RNA from circulating tumor cells obtained from a subject, determining the expression of at least one biomarker RNA molecule in the isolated RNA and providing an expression profile based on the results;
  (B) isolating RNA from extracellular vesicles obtained from the subject, determining the expression of at least one biomarker RNA molecule in the isolated RNA and providing an expression profile based on the results; and
  (C) using the expression profiles determined in (A) and determined in (B) for a combined analysis of the results.

The present method considers the expression profile obtained for circulating tumor cells and the expression profile obtained for extracellular vesicles for a combined analysis and evaluation of the results. This combined analysis can provide complementary as well as supporting information which increases the significance of the obtained results. For such combined analysis, a combined expression profile can be e.g. provided based on the CTC expression profile and the EV expression profile. As is demonstrated by the examples, a combined analysis of the CTC and EV expression profiles enhances the prognostic and predictive value of the obtained results and can provide valuable diagnostic, prognostic and/or predictive information. The present in vitro method can thus be used as improved diagnostic, prognostic and/or predictive aid in the management of cancer patients. It can be used to support the diagnosis, prognosis or to choose the most appropriate treatment for cancer patients. The present method therefore provides an improved method for the analysis of RNA biomarkers and makes an important contribution to the art.

According to a second aspect a method for determining the effectiveness of a therapy in a subject or for predicting or monitoring therapy response in a patient is provided, comprising determining the expression level of AURKA in extracellular vesicles and optionally circulating tumor cells. As is demonstrated by the examples and explained herein, detection of AURKA expression provides valuable information. It is referred to the respective disclosure.

Other objects, features, advantages and aspects of the present application will become apparent to those skilled in the art from the following description and appended claims. It should be understood, however, that the following description, appended claims, and specific examples, while indicating preferred embodiments of the application, are given by way of illustration only. Various changes and modifications within the spirit and scope of the disclosed invention will become readily apparent to those skilled in the art from reading the following.

BRIEF DESCRIPTION OF THE FIGURES

FIG. 1A shows the results for HER2 expression in CTCs. FIG. 1B shows the results for HER2 or HER3 expression in CTCs. FIG. 1C shows the results for expression of at least one of the TKs in CTCs. FIG. 1D shows the results for expression of at least one of the TKs in CTCs or EVs.

FIG. 2A shows the results for samples positive for AURKA in EVs. FIG. 2B shows the results for samples negative for AURKA in EVs.

FIG. 3A shows the results for mTOR expression in CTCs. FIG. 3B shows the results for mTOR expression in EVs.

FIG. 5 shows Table I.

DETAILED DESCRIPTION OF THE INVENTION

Figure 1:
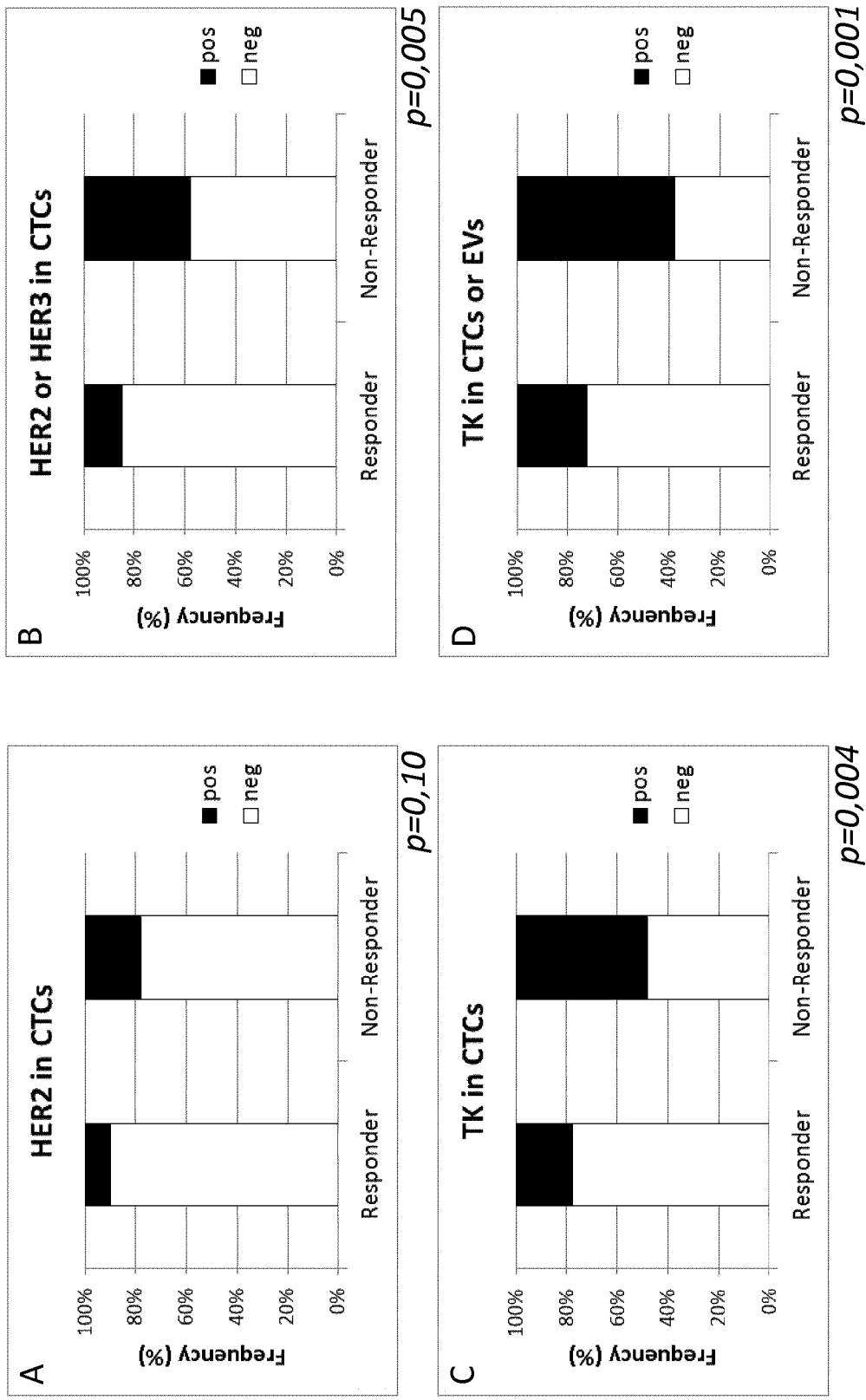
FIGS. 1A to 1D show the relation of TK (HER2, HER3, cMet or cKit) expression to therapy response in MBC patients (Example 2). The graphs depict the frequency of biomarker positive (pos) and biomarker negative (neg) samples within the groups of Responders and Non-Responders.

According to a first aspect, a method for analyzing the expression of one or more biomarker RNA molecules is provided, comprising (A) isolating RNA from circulating tumor cells obtained from a subject, determining the expression of at least one biomarker RNA molecule in the isolated RNA and providing an expression profile based on the results;

(B) isolating RNA from extracellular vesicles obtained from the subject, determining the expression of at least one biomarker RNA molecule in the isolated RNA and providing an expression profile based on the results; and (C) using the expression profiles determined in (A) and determined in (B) for a combined analysis of the results.

Each individual step of the method as well as suitable and preferred embodiments of the present method are subsequently described in detail.

Step (A)

In step (A), RNA is isolated from circulating tumor cells (CTC) obtained from a subject and the expression of at least one biomarker RNA molecule in the isolated RNA is determined and an expression profile is provided based on the results. Thereby, a CTC expression profile is provided which comprises the results of the at least one biomarker RNA molecule.

As discussed also in detail below, it is preferred to determine the expression of multiple biomarker RNA molecules, e.g. a biomarker panel, in parallel to increase the informative value of the CTC expression profile. Accordingly, in embodiments, step (A) comprises determining the expression of at least 2, at least 3, at least 5, at least 7, at least 10, at least 12, at least 15, at least 17 or at least 20 biomarker RNA molecules. The CTC expression profile provided in step (A) accordingly may comprise the expression results of at least 2, at least 3, at least 5, at least 7, at least 10, at least 12, at least 15, at least 17 or at least 20 biomarker RNA molecules. Further embodiments are also described subsequently. As discussed herein, expression of the same biomarker RNA molecules can be determined in step (A) and step (B). However, it is also within the scope of the present disclosure to analyse different biomarker RNA molecules in step (A) and step (B). Details regarding exemplary suitable and preferred embodiments for the biomarker RNA molecules and biomarker RNA panels are described below and it is referred to the respective disclosure.

Exemplary suitable and preferred embodiments for isolating RNA from circulating tumor cells and determining the biomarker RNA expression are described below and it is referred to the respective disclosure.

Step (B)

In step (B), RNA is isolated from extracellular vesicles (EV) obtained from a subject and the expression of at least one biomarker RNA molecule in the isolated vesicular RNA is determined and an expression profile is provided based on the results. Thereby, an EV expression profile is provided which comprises the results of the at least one biomarker RNA molecule.

As discussed also in detail below, it is preferred to determine the expression of multiple biomarker RNA molecules, e.g. a biomarker panel, in parallel to increase the informative value of the EV expression profile. Accordingly, in embodiments, step (B) comprises determining the expression of at least 2, at least 3, at least 5, at least 7, at least 10, at least 12, at least 15, at least 17 or at least 20 biomarker RNA molecules. The EV expression profile provided in step (B) accordingly may comprise the expression results of at least 2, at least 3, at least 5, at least 7, at least 10, at least 12, at least 15, at least 17 or at least 20 biomarker RNA molecules. Further embodiments are also described subsequently. As discussed herein, expression of the same biomarker RNA molecules can be determined in step (B) and step (A). However, it is also within the scope of the present disclosure to analyse different biomarker RNA molecules in step (B) and step (A). Details regarding exemplary suitable and preferred embodiments for the biomarker RNA molecules and biomarker RNA panels are described below and it is referred to the respective disclosure.

Exemplary suitable and preferred embodiments for isolating RNA from extracellular vesicles and determining the biomarker RNA expression are described below and it is referred to the respective disclosure.

Step (C)

Step (C) comprises using the expression profiles determined in (A) and determined in (B) for a combined analysis of the results. As discussed herein and demonstrated in the examples, such combined analysis, which considers the results from the CTC expression profile and the results from the EV expression profile, improves the significance and thus the value of the obtained diagnostic, prognostic and/or predictive information. It allows taking into account complementary as well as additive information that is provided by the CTC and EV expression profiles. The results that are provided based on such combined analysis as it is taught by the present invention are therefore significantly improved compared to an analysis that considers the results of either the CTC expression profile or the results of the EV expression profile. Exemplary suitable and preferred uses of the combined analysis are described below.

According to one embodiment, the combined analysis comprises providing a combined expression profile using the expression profile determined in (A) and the expression profile determined in (B). Accordingly, in such combined analysis, the CTC expression profile that is provided in step (A) and the EV expression profile that is provided in (B) are used to provide a combined expression profile that comprises expression results from the CTC expression profile and the EV expression profile. The provided combined expression profile can be advantageously used as diagnostic, prognostic and/or predictive aid in the management of cancer patients. It can be used to support the diagnosis, prognosis or to choose the most appropriate treatment for cancer patients. Exemplary suitable and preferred embodiments for creating such combined expression profile and exemplary suitable and preferred uses thereof are described below.

Embodiments of Step (A) and (B)

To provide circulating tumor cells and extracellular vesicles for the analysis, a biological sample comprising circulating tumor cells and extracellular samples, such as e.g. blood, can be collected from the subject. By collecting an according biological sample, it is ensured that the circulating tumor cells and the extracellular vesicles are obtained from the subject at the same time point. Exemplary suitable and preferred embodiments are described in the following:

According to one embodiment, the present method comprises
providing a liquid biological sample obtained from the subject;
removing cells from the liquid biological sample, thereby providing a cell-depleted biological sample;
isolating circulating tumor cells from the removed cells;
wherein step (A) comprises isolating RNA from the isolated circulating tumor cells;
wherein step (B) comprises isolating RNA from extracellular vesicles comprised in the cell-depleted biological sample.

In this embodiment, cells are removed from the liquid biological sample (e.g. blood), thereby providing a cell-depleted biological sample (e.g. plasma in case of blood). Circulating tumor cells are then isolated from the removed cell fraction. Exemplary suitable and preferred CTC isolation methods are also described below. In step (A), RNA is then obtained from the isolated and thus enriched CTCs. In step (B), vesicular RNA is isolated from the cell-depleted biological sample. Advantageously, this embodiment allows the isolation of CTC RNA and vesicular RNA from the same obtained biological sample. It allows to use the full collected volume for CTC isolation and vesicular RNA isolation. This is advantageous considering that CTCs are often rare so that it is desirous to process larger sample volumes.

According to one embodiment, the method comprises
providing a liquid biological sample obtained from the subject;
isolating circulating tumor cells from the liquid biological sample;
removing remaining cells from the liquid biological sample from which the circulating tumor cells were isolated thereby providing a cell-depleted biological sample;
wherein step (A) comprises isolating RNA from the isolated circulating tumor cells;
wherein step (B) comprises isolating RNA from extracellular vesicles comprised in the cell-depleted biological sample.

In this preferred embodiment, CTCs are removed from the liquid biological sample (e.g. blood), thereby providing a biological sample from which CTCs were depleted. Remaining cells are then removed to provide a cell-depleted biological sample (e.g. plasma in case of blood). In step (A), RNA is then isolated from the isolated and thus enriched CTCs. In step (B), vesicular RNA is isolated from the cell-depleted biological sample. Also this embodiment allows the isolation of CTC RNA and vesicular RNA from the same obtained biological sample. Moreover, as the CTCs are isolated from the biological sample first, the overall handling time of the CTCs is reduced which is advantageous to prevent damage to these rare and thus precious cells.

According to a further embodiment, the method comprises
providing at least two liquid biological samples of the same kind obtained from the same subject;
isolating circulating tumor cells from at least one of the liquid biological samples, wherein step (A) comprises isolating RNA from the isolated circulating tumor cells;
obtaining a cell-depleted sample from at least one of the liquid biological samples, wherein step (B) comprises isolating RNA from extracellular vesicles comprised in the cell-depleted biological sample.

In this embodiment, at least two liquid biological samples of the same kind (e.g. blood) are provided that were obtained from the same subject at the same time. E.g. the at least two biological samples of the same kind can be obtained by aliquoting a (single) biological sample that has been collected from the subject. E.g. a collected blood sample can be divided into two aliquots, wherein one aliquot is processed and used for isolation of the CTC RNA and the other aliquot is processed and used for isolation of vesicular RNA. According to a further embodiment, the at least two biological samples of the same kind were obtained from the same subject at the same time, e.g. by drawing at least two blood samples at the same collection time, wherein one sample is processed and used for isolation of the CTC RNA and the other sample is processed and used for isolation of vesicular RNA.

According to one embodiment, which applies to all three embodiments discussed above, the method comprises isolating extracellular vesicles from the cell-depleted sample and step (B) comprises isolating RNA from the isolated extracellular vesicles. This embodiment is advantageous because it increases the specificity for the extracellular vesicles. However, it is also within the scope of step (B) to isolate RNA from extracellular vesicles comprised in the cell-depleted biological sample directly from the cell-depleted biological sample without prior isolation and thus enrichment of extracellular vesicles. This embodiment is also feasible because it is assumed that most of the RNA comprised in the cell-depleted biological sample and thus isolated therefrom originates from extracellular vesicles such as exosomes. Preferably, the extracellular vesicles are isolated though from the cell-depleted biological sample (e.g. blood plasma or serum) and vesicular RNA is then isolated in step (B) from the isolated and thus enriched extracellular vesicles. Exemplary suitable and preferred methods for isolating extracellular vesicles such as exosomes are also described below.

CTCs and Isolation of CTCs

Circulating tumor cells (CTCs) are well known in the art. Commonly, CTCs are cells that have shed into the vasculature or lymphatic from a primary tumor and are carried around the body in the circulation. CTCs can be shed actively or inactively. They can circulate in the blood and lymphatic system as single cells or as aggregates, so called circulating tumor microemboli. CTCs thus originate from the primary tumor and can constitute living seeds for the subsequent growth of additional tumors (metastases) in vital distant organs. Therefore, CTCs can trigger a mechanism that is responsible for the vast majority of cancer-related deaths. CTCs can also originate from metastases. CTCs have been identified in many different cancers and it is widely accepted that CTCs found in peripheral blood originate from solid tumors and are involved in the haematogenous metastatic migration of solid tumors to distant sites. The term CTC as used herein in particular includes circulating cells derived from all types of tumors, especially of solid tumors, in particular of metastasizing solid tumors. The term CTC as used herein inter alia includes but is not limited to CTCs that are confirmed cancer cells with an intact, viable nucleus that express cytokeratins or epithelial marker molecules like EpCam and have an absence of CD45; cytokeratin negative (CK−) CTCs that are cancer stem cells or cells undergoing epithelial-mesenchymal transition (EMT) which may lack expression of cytokeratins or epithelial markers like EpCam and CD45; apoptotic CTCs that are traditional CTCs that are undergoing apoptosis (cell death); small CTCs that usually are cytokeratin positive and CD45 negative, but with sizes and shapes similar to white blood cells, dormant CTCs, as well as CTC clusters of two or more individual CTCs, e.g. of any of the aforementioned types of CTCs or a mixture of said types of CTCs are bound together. The CTC cluster may contain e.g. traditional, small and/or CK− CTCs.

CTCs are generally very rare cells within a bodily fluid. For example, CTCs may be found in frequencies on the order of 1-10 CTCs per 5 mL of whole blood in patients with primary cancer but can be sometimes found in higher numbers up to 1000/5 ml blood in metastatic cancer. To provide information on CTCs, the isolation and thus enrichment of tumor cells or the removal of other nucleated cells in blood is required. Any method can be used in conjunction with the present method that is suitable to isolate and thus enrich circulating tumor cells from a sample (e.g. the biological sample or the cells removed from the biological sample, see above). The term "isolating" is used herein a broad sense and encompasses e.g. any form of enrichment or purification of circulating tumor cells from a sample. Because CTCs are often rare, common CTC isolation procedure usually co-isolate other cell types together with the desired CTCs so that isolated CTCs are comprised to a certain extent in the background of normal cells. Such methods nevertheless enrich and thus isolate CTCs and therefore are methods for isolating CTCs. Methods for isolating circulating tumor cells from various biological samples are well known in the art therefore need no detailed description herein. Exemplary suitable methods are briefly described in the following.

CTCs may be enriched and thus isolated using various physical and/or affinity capture based methods. CTCs may be isolated by methods that include a positive selection of CTC cells, e.g. by a method directly targeting CTCs, or methods that include a negative selection, e.g. by depleting non-CTC cells (e.g. leukocytes in case of blood). Also feasible are methods that enrich and thus isolate CTCs by size using e.g. filtration based methods, deformability or density or other physical methods. Moreover, a combination of the aforementioned methods can be used.

According to a preferred embodiment, circulating tumor cells are isolated by affinity capture. Such affinity based capture methods specifically bind CTCs to a surface (e.g. a bead, membrane or other surface). Specificity for CTCs is achieved by using one or more binding agents (e.g. antibodies) that bind to structures, e.g. epitopes or antigens, present on the CTCs. In embodiments, said one or more binding agents bind tumor-associated markers present on the CTCs. E.g. CTCs may be isolated using antibody-coated solid phase (e.g. magnetic beads) that can capture CTC cells. For CTC capture, a combination of two or more antibodies can be used that bind with high specificity and affinity to epitopes or antigens on the desired CTC cells. Binding agents may also be selected to target epitopes or antigens present on the CTCs depending on the tumor type. E.g. different structures, e.g. epitopes or antigens, may be present on the CTCs that can be targeted by the binding agent (e.g. antibody) depending on the primary tumor type, also taking potential EMT or tumor stemcell phenotype changes into consideration. The use of an according binding agent (e.g. antibody) based capturing platform is advantageous since it may also enrich CTCs which have undergone phenotype changes in the course of e.g. epithelial to mesenchymal transition (EMT) or display tumor-stemness. According to a preferred embodiment, the epitopes targeted by the binding agent are epithelial- and/or tumor-associated antigens, such as e.g. EpCAM, EGFR and HER2. A commercially available system for isolating circulating tumor cells is the AdnaTest (QIAGEN).

Another method that is based on positive selection and therefore represents a suitable CTC isolation method for obtaining CTCs is based on the enumeration of epithelial cells that are separated from blood by antibody-magnetic nanoparticle conjugates that target epithelial cell surface markers, EpCAM, and the subsequent identification of the CTCs with fluorescently labeled antibodies against cytokeratin (CK 8, 18, 19) and a fluorescent nuclear stain. An according method is used in the commercially available system of CellSearch (Menarini/Veridex LLC). Other known methods for CTC enrichment and thus CTC isolation include but are not limited to Epic sciences method, the ISET Test, the use of a Microfluidic cell sorter (pFCS which employs a modified weir-style physical barrier to separate and capture CTCs e.g. from unprocessed whole blood based on their size difference), ScreenCell (a filtration based device that allows sensitive and specific isolation of CTCs e.g. from human whole blood), Clearbridge, Parsortix and IsoFlux.

RNA can then be isolated from the isolated circulating tumor cells. Exemplary and preferred methods for RNA isolation are described herein.

Extracellular Vesicles and Isolation of Extracellular Vesicles

The term extracellular vesicle (EV) as used herein in particular refers to any type of secreted vesicle of cellular origin. Extracellular vesicles (EVs) may be broadly classified into exosomes, microvesicles (MVs) and apoptotic bodies. Extracellular vesicles such as exosomes and microvesicles are small vesicles secreted by cells. EVs have been found to circulate through many different body fluids including blood and urine which makes them easily accessible. Due to the resemblance of EVs composition with the parental cell, circulating EVs are a valuable source for biomarkers. Circulating EVs are likely composed of a mixture of exosomes and MVs.

They contain stable nucleic acids (e.g. mRNA, miRNA, other small RNAs), DNA and protein, protected from degradation by a lipid bilayer. The contents are accordingly specifically packaged, and represent mechanisms of local and distant cellular communications. They can transport RNA between cells. EVs such as exosomes are an abundant and diverse source of circulating biomarkers. The cell of origin may be a healthy cell or a cancer cell. EVs such as exosomes are often actively secreted by cancer cells, especially dividing cancer cells. As part of the tumor microenvironment, EVs such as exosomes seem to play an important role in fibroblast growth, desmoplastic reactions but also initiation of epithelial-mesenchymal transition (EMT) and SC as well as therapy resistance building and initiation of metastases and therapy resistance. Exosomes are smaller than CTCs and comprise a lower number of copies per biomarker. Compared to CTCs, EVs are easier accessible because they are present in very large numbers in body fluids such as for example approx. $10^9$-$10^{12}$ vesicles per ml of blood plasma.

As discussed above, the present method comprises in one embodiment the isolation of extracellular vesicles prior to RNA isolation. Any method can be used in conjunction with the present method that is suitable to isolate and thus enrich extracellular vesicles from a sample. The sample is as described above preferably a cell-depleted biological sample (e.g. plasma). The term "isolation" is again used in a broad sense and covers the enrichment or purification of extracellular vesicles. Extracellular vesicles can be isolated from virtually any biofluid after removing cellular components. Suitable methods for isolating extracellular vesicles such as exosomes are known in the art and therefore, need no detailed description herein. Exemplary suitable methods for isolating extracellular vesicles are briefly described herein.

Extracellular vesicles, including exosomes, can be isolated from cell-depleted body fluids, such as for example blood plasma or serum. E.g. extracellular vesicles may be isolated by ultracentrifugation, ultrafiltration, gradients and affinity capture or a combination of according methods. Numerous protocols and commercial products are available for extracellular vesicle/exosome isolation, and are known to the skilled person. Exemplary, non-limiting isolation methods are described in the following.

Extracellular vesicles and in particular exosomes can be isolated e.g. by methods involving ultracentrifugation. An exemplary ultracentrifugation isolation method is described by Thery et al. (Isolation and Characterization of Exosomes from Cell Culture Supernatants and Biological Fluids. Unit 3.22, Subcellular Fractionation and Isolation of Organelles, in Current Protocols in Cell Biology, John Wiley and Sons Inc., 2006). Hence according to one embodiment, extracellular vesicles are isolated by ultracentrifugation.

To increase the purity of the isolated extracellular vesicles, cells and cell fragments, and optionally apoptotic bodies if desired, can be removed prior to isolating the extracellular vesicles, e.g. by centrifugation or filtration. E.g. filtration methods can be used which exclude particles larger than 0.8 µm, 0.7 µm or 0.6 µm.

According to one embodiment, extracellular vesicles are isolated by affinity capture to a solid phase. According to one embodiment, extracellular vesicles, such as exosomes, are isolated by immuno-magnetic capture using magnetic beads coated with antibodies directed against proteins exposed on extracellular vesicles, e.g. on exosomal membranes.

According to one embodiment, extracellular vesicles are captured by passing the cell-depleted sample through a vesicle capture material. Bound extracellular vesicles can be washed and subsequently eluted. Commercial systems that are based on affinity capture such as the exoEasy Kit (QIAGEN) are available for extracellular vesicle purification and can be used in conjunction with the present invention.

Methods based on the use of volume-excluding polymers, such as PEG, have also been described for the isolation of EVs. Therein, the polymers work by tying up water molecules and forcing less-soluble components such as extracellular vesicles out of solution, allowing them to be collected by a short, low-speed centrifugation. Commercial products that make use of this principle are ExoQuick (System Biosciences, Mountain View, USA) and Total Exosome Isolation Reagent (Life Technologies, Carlsbad, USA). Hence according to one embodiment, extracellular vesicles are isolated by precipitation with a volume-excluding polymer. Also, extracellular vesicles, such as exosomes, can be isolated based on their density, e.g. by layering the sample onto discontinuous sucrose or iodixanol gradients and subjecting to high speed centrifugation. Thus according to one embodiment, extracellular vesicles, such as exosomes, are isolated by density gradient centrifugation.

According to one embodiment, the extracellular vesicles comprise or predominantly consist of exosomes and/or microvesicles. According to one embodiment, the extracellular vesicles comprise or predominantly consist of exosomes.

RNA can then be isolated from the isolated extracellular vesicles, such as in particular the isolated exosomes. Exemplary and preferred methods for RNA isolation are described herein.

Isolation of RNA in Step (A) and/or Step (B)

The present method comprises the isolation of RNA from circulating tumor cells in step (A) and the isolation of RNA from extracellular vesicles in step (B). As discussed above, circulating tumor cells and extracellular vesicles may be isolated from a biological sample obtained from a subject prior to RNA isolation. The term "isolation" is again used in a broad sense and encompasses e.g. the enrichment or purification of RNA. Suitable RNA isolation methods that can be used in step (A) and/or step (B) are known to the skilled person and therefore, do not need detailed description herein. Exemplary embodiments are nevertheless illustrated in the following.

Methods, e.g. based on the use of phenol and/or chaotropic salts, can be used for RNA isolation. Examples of suitable methods include, but are not limited to, extraction, solid-phase extraction, polysilicic acid-based purification, magnetic particle-based purification, phenol-chloroform extraction, anion-exchange chromatography (using anion-exchange surfaces), electrophoresis, precipitation and combinations thereof. According methods are well known in the art. In case DNA is isolated together with the RNA, it can be removed e.g. by DNase digestion. Methods are also known in the art that specifically isolate RNA, essentially free from DNA contaminations. As discussed, remaining DNA can moreover be removed by DNase digestion and/or intron spanning primers can be used in case expression of the biomarker RNA molecule is detected by amplification.

An example of a phenol/chloroform-based organic extraction method for the isolation of RNA is the Chomczynski method (Chomczynski and Sacchi, 1987: Single-step method of RNA isolation by acid guanidinium thiocyanate-phenol-chloroform extraction. Anal. Biochem. (162): 156-159) and variations thereof. According to said method, the RNA is concentrated during phenol/chloroform extraction in the aqueous phase and is then subsequently isolated therefrom e.g. by adding alcohol to the aqueous phase and binding the RNA to a nucleic acid binding solid phase. An example of a phenol/chloroform based commercial product is the miRNeasy Mini kit (QIAGEN). It provides high quality and high yields of total RNA including small RNA from various different biological samples.

According to one embodiment, RNA isolation in step (A) and/or step (B) comprises binding RNA to a solid phase and eluting the RNA from the solid phase. The RNA may be washed prior to elution. Suitable solid phases and compatible chemistries to achieve RNA binding to the solid phase are known to the skilled person and include but are not limited to silica solid phases and solid phases with anion exchange moieties.

According to one embodiment, RNA isolation in step (A) and/or step (B) comprises binding RNA to a solid phase, such as in particular a silica solid phase, wherein at least one chaotropic agent and/or at least one alcohol are used for RNA binding. As is known, chaotropic salts include but are not limited to guanidinium salts such as guanidinium hydrochloride, guanidinium thiocyanate (or guanidinium isothiocyanate (GITC)) or chaotropic salts comprising thiocyanate, iodide, perchlorate, trichloroacetate or trifluroacetate and the like. Also mixtures of chaotropic salts may be used. Such chaotropic salts can be provided e.g. as sodium or potassium salts. Alcohols that frequently are used for RNA isolation include branched or unbranched aliphatic alcohols with 1 to 5 carbon atoms and may be selected from methanol, ethanol, propanol, isopropanol and butanol and mixtures thereof. Suitable concentrations of chaotropic agents and alcohols are known to the skilled person and do not require a detailed description here. The bound RNA may optionally be washed. Either prior to or subsequent to the optional washing step, a DNase digest may be performed. Such DNase digest may be performed e.g. while the RNA is bound to the nucleic acid binding solid phase. Suitable embodiments for performing a respective DNase digest are known in the prior art. Elution can be achieved for example with classical elution solutions such as water, elution buffers, in particular low salt elution buffers. The elution buffers may comprise a biological buffer such as Tris, MOPS, HEPES, MES, BIS-TRIS propane and others. Preferably, elution solutions are used that do not interfere with the intended downstream applications.

According to one embodiment, RNA isolation in step (A) and/or step (B) comprises binding RNA to a solid phase with anion exchange moieties and eluting the RNA from the solid phase. In particular, isolation methods that are based on the charge-switch principle may be used. Examples of suitable solid phases with anion exchange moieties comprise, but are not limited to, materials, such as particulate materials or columns, that are functionalized with anion exchange groups. Examples of anion exchange moieties are monoamines, diamines, polyamines, and nitrogen-containing aromatic or aliphatic heterocyclic groups. The RNA is bound to the solid phase at binding conditions that allow binding of the RNA to the anion exchange moieties. To that end, suitable pH and/or salt conditions can be used, as is known to the skilled person. The bound RNA can optionally be washed. Any suitable elution method can be used and suitable embodiments are known to the skilled person. Elution can e.g. involve changing the pH value. Thus, elution can e.g. occur at an elution pH which is higher than the binding pH. Likewise, ionic strength can be used to assist or effect the elution. Elution can also be assisted by heating and/or shaking.

The isolated CTCs in step (A) and/or the isolated extracellular vesicles in step (B) can be lysed to liberate the RNA from the cells or the extracellular vesicles for RNA isolation. According to one embodiment, RNA isolation comprises the lysis of the isolated CTCs in step (A) to liberate the RNA from the cells. According to one embodiment, RNA isolation comprises the lysis or digestion of the isolated extracellular vesicles in step (B) to liberate the RNA from the vesicles such as the exosomes.

Suitable lysis methods are known to the skilled person and thus need no detailed description herein. Different methods can be used for lysis, and suitable lysis methods are well-known in the prior art. The CTCs and/or the extracellular vesicles can be contacted for disruption, respectively lysis, with one or more lysing agents. These can be contained in a disruption reagent such as a lysis buffer. RNA should be protected during lysis from degradation by nucleases. Generally, the lysis procedure may include but it is not limited to mechanical, chemical, physical and/or enzymatic actions on the sample. Examples include but are not limited to homogenising, the application of ultrasound, heating, the addition of one or more detergents and/or the addition of one or more protein degrading compounds, such as for example protein degrading enzymes or salts. Furthermore, reducing agents such as beta-mercaptoethanol or DTT can be added for lysis to assist denaturation of e.g. nucleases. According to one embodiment, at least one chaotropic agent, such as preferably at least one chaotropic salt, is used for lysing and hence disruption. Suitable chaotropic agents and in particular suitable chaotropic salts are known to the skilled person and are also described herein.

According to one embodiment, total RNA is isolated from the CTC lysate. According to one embodiment, mRNA is then isolated from the total CTC derived RNA, e.g. by oligo d(T) capture or other suitable methods.

According to one embodiment, total RNA is isolated from the extracellular vesicle lysate/digest. According to one embodiment, mRNA is then isolated from the total vesicular RNA, e.g. by oligo d(T) capture or other suitable methods.

According to one embodiment, the RNA isolated in step (A) and/or step (B) comprises or consists of mRNA. The method therefore encompasses the purification of RNA that comprises mRNA (among other RNA types) as well as the selective purification of mRNA. Essentially pure mRNA can be obtained e.g. by using RNA isolation methods which selectively isolate mRNA (but not other RNA types) from the digested sample. Purified mRNA can also be isolated sequentially, e.g. by first isolating total RNA, followed by selectively isolating mRNA from the isolated total RNA. Suitable methods for selective mRNA isolation are known to the skilled person and therefore, do not need detailed description. A well-established method is based on oligo(dT) capture to a solid phase (e.g. a column or magnetic beads), which allows to specifically isolates mRNA via its poly(A) tail.

According to one embodiment, the RNA isolated in step (A) and/or step (B) comprises miRNA or essentially consists of small RNA up to 350 nt in length, up to 250 nt length or up to 200 nt in length, which includes miRNA. The method therefore encompasses the purification of RNA that comprises miRNA (among other RNA types) as well as the specific purification of small RNA molecules that comprise miRNA but is depleted of large RNA molecules (e.g. having a length of 400 nt or larger). Suitable methods for enriching specifically small RNA molecules separately from large RNA molecules are well-known in the prior art and therefore, do not need to be described herein.

Determining the Expression of the at Least One Biomarker RNA Molecule

As discussed above, in step (A) and step (B) expression of the one or more biomarker RNA molecules analysed is determined. Thereby, it can be e.g. determined whether the biomarker RNA molecule is differentially expressed in CTCs and/or EVs of the subject. A differential expression can be for example the overexpression of the corresponding biomarker RNA molecule compared to the expression of said biomarker RNA molecule in a control (for example a healthy subject). In one embodiment, overexpression comprises the de novo expression of a biomarker RNA molecule in the subject. A differential expression can also be seen in the absence or down-regulation of the expression of an according biomarker RNA molecule so that it is not expressed or expressed to a lower extent in the CTCs and/or EVs compared to a control or reference sample. Therefore, it is advantageous to determine the expression level of the one or more biomarker RNA molecules in step (A) and in step (B).

Any method suitable to determine the expression of a biomarker RNA molecule can be used in the present method. According methods are well-known to the skilled person and therefore, need no detailed description herein. Exemplary suitable and preferred methods are described briefly in the following.

According to one embodiment, determining the expression of the at least one biomarker RNA molecule in the isolated RNA in step (A) and/or step (B) comprises reverse transcription to obtain cDNA. The isolated RNA can be reverse transcribed to cDNA by using a reverse transcription polymerase. Providing cDNA is advantageous, because cDNA is more stable than RNA and can be easily used e.g. in amplification reactions. Suitable methods for reverse transcription are well-known in the art and therefore, need no detailed description herein.

According to one embodiment, determining the expression of the at least one biomarker RNA molecule in the isolated RNA in step (A) and/or step (B) comprises at least one step of amplification, e.g. by amplifying the cDNA. Suitable amplification methods are well-known to the skilled person and therefore, need no detailed description herein. Preferred is performing a polymerase chain reaction as amplification reaction. The amplification provides amplicons corresponding to the one or more biomarker RNA molecules tested for. Suitable primers for amplification can be determined by the skilled person. According to one embodiment, expression of two or more biomarker RNA molecules is determined in parallel by performing a multiplex-PCR using obtained cDNA as template. Suitable primers for amplification can be determined by the skilled person.

Moreover, the reverse transcription step can be combined with an amplification step by performing e.g. a reverse transcription polymerase chain reaction. Suitable embodiments are well-known in the art and therefore, need no detailed description herein.

According to one embodiment, determining the expression of the at least one biomarker RNA molecule in the isolated RNA in step (A) and/or step (B) comprises performing a quantitative polymerase chain reaction. In one embodiment, a semi-quantitative PCR is performed. In another embodiment, the method is not semi-quantitative. Performing a quantitative PCR (qPCR) is advantageous because it allows to determine whether the biomarker RNA molecule is for example overexpressed in CTCs and/or EVs. Suitable methods for performing a quantitative PCR are well-known to the skilled person and therefore, need no detailed description herein. The Ct values obtained in the quantitative PCR for the individual one or more marker RNA molecules analysed can then be recorded and used for providing the expression profile.

By performing a quantitative amplification analysis, the expression level can be determined and it can be analyzed whether a certain biomarker RNA molecule is overexpressed or not in the analyzed sample. According to one embodiment, a real-time qPCR is performed to determine, e.g. based on the Ct value, the expression level of the at least one biomarker RNA molecule.

As is demonstrated in the examples, in one embodiment, it is determined whether a biomarker RNA molecule is overexpressed or not. If several biomarker RNA molecules (e.g. a biomarker panel) are analysed for providing the expression profile, what is preferred, it can be determined whether two or more, five or more or preferably all biomarker RNA molecules analysed are overexpressed in the CTCs and/or EVs, preferably CTCs and EVs. The results (e.g. overexpression: yes/no) can be included in the expression profiles that are provided in step (A) and (B) and can then be used in the combined analysis in step (C). According to one embodiment, a quantitative reverse transcription PCR is performed.

The cDNA can be amplified with primers that are specific for the cDNA of the at least one biomarker RNA molecule. Suitable primers for amplification can be determined by the skilled person. According to one embodiment, the cDNA is contacted with sense and anti-sense primers that are specific for the at least one biomarker and moreover a DNA polymerase in order to generate amplified DNA.

To improve the specificity in the amplification reaction, intron-spanning primers can be used. This prevents a co-amplification of DNA contaminations that might be present in the RNA preparation. Additionally or alternatively, e.g. in case intron-spanning primers are not available, a DNase digest can be performed on the RNA prior to reverse transcription to remove according DNA contaminations in the RNA preparation and hence the isolated RNA.

According to one embodiment, a pre-amplification step is performed after the reverse transcription step and prior to performing a quantitative PCR reaction. Such pre-amplification step can improve the sensitivity. This can be advantageous considering that CTCs are often rare. Depending on the biological sample, often merely one to twenty or just one to ten circulating tumor cells can be isolated. By pre-amplifying the cDNA molecules that correspond to the analyzed one or more biomarker RNA molecules, more DNA material is provided for the subsequent amplification step, which preferably is a qPCR. This can improve the results of the quantitative PCR. When performing an according pre-amplification step it should be ensured that the specificity of the subsequent quantitative PCR is not impaired or prejudiced. According methods are known to the skilled person and accordingly, need no detailed description herein.

According to one embodiment, determining the expression of the at least one biomarker RNA molecule in the isolated RNA in step (A) and/or step (B) comprises determining whether the at least one biomarker RNA molecule is overexpressed. According to this preferred embodiment it is determined, whether the one or more biomarker RNA molecules are overexpressed in CTCs and/or EVs or not. Suitable methods for determining overexpression of a RNA marker are known to the skilled person and therefore need no detailed description herein. Exemplary suitable and preferred methods are nevertheless described in the following.

According to one embodiment, determining the expression of at least one biomarker RNA molecule in the isolated RNA in step (A) and/or step (B) comprises determining whether the expression level of the at least biomarker RNA molecule is higher than the expression level of that biomarker RNA molecule in a control or reference, e.g. determined in a healthy control or reference group if the subject is a cancer patient. The present method also encompasses in embodiments determining in step (A) and/or (B) whether the expression level of at least one biomarker RNA molecule is lower than the expression level of that biomarker RNA molecule in a control or reference, e.g. again determined in a healthy control or reference group if the subject is a cancer patient.

According to one embodiment, a biomarker RNA molecule is determined to be overexpressed if its expression exceeds a defined threshold, also referred to herein as cut-off. E.g. if in step (A) the expression level of said biomarker RNA molecule is determined to be above a defined threshold, the expression profile in (A) indicates that the CTCs are positive for said biomarker RNA molecule. If in step (B) the expression level of said biomarker RNA molecule is determined to be above a defined threshold, the expression profile in (B) indicates that the extracellular vesicles are positive for said biomarker RNA molecule.

The threshold/cut-off is preferably set so that the assay achieves a specificity for the at least one biomarker RNA molecule of at least 85%, preferably at least 90%. An exemplary suitable way to determine the threshold is explained in the following. When analyzing the expression of a biomarker RNA molecule in CTCs obtained from a cancer patient, the threshold can be defined by determining the mean expression of said biomarker in a healthy donor population of a suitable size (e.g. n=15-50, e.g. n=20). E.g. when isolating CTCs from a blood sample of a cancer patient for analysis, blood from healthy donors can be used as reference. The expression of said biomarker RNA molecule is determined in each healthy donor and a mean expression is calculated for each biomarker RNA molecule. For determining the threshold for each biomarker RNA molecule, the determined mean value e.g. plus a relevant standard deviation is considered. A threshold determined by the mean value plus a relevant standard deviation (e.g. 1× standard deviation) can then be double-checked to determine whether the threshold is set high/stringent enough to achieve the desired specificity of e.g. at least 90%. This can be e.g. double-checked by applying the threshold to the expression results obtained for each healthy donor of the healthy donor population used. If the biomarker RNA molecule is determined to be overexpressed in more than 10% of the healthy donors, the threshold/cut-off is not stringent enough and must be increased to achieve 90% specificity (e.g. by setting the threshold to mean value plus 2× standard deviation). Thereby, a suitable threshold can be calculated for each biomarker RNA molecule to be analysed. Therefore, in one embodiment, the method comprises applying different thresholds/cut-offs for the biomarker RNA molecules analysed. An according method can also be applied for determining the threshold for expression in EVs. E.g. when isolating vesicular RNA from plasma of a cancer patient for analysis (either with or without prior isolation of the extracellular vesicles from the plasma), plasma from healthy donors can be used as reference. Different thresholds/cut-offs may need to be applied for a biomarker RNA molecule depending on whether expression is determined in CTCs or EVs.

According to one embodiment, expression of the biomarker RNA molecule is determined by performing a quantitative PCR, which provides a Ct value for the biomarker RNA molecule analysed. The lower the Ct value, the higher is the expression of the biomarker RNA molecule. For determining overexpression compared to the reference/control threshold/cut-off (which can be e.g. determined as described above), the $\Delta Ct$ can be taken into consideration, e.g. $\Delta Ct = (CutOff_{(gene)} - SampleCt_{(gene)})$. If the $\Delta Ct$ is above 0, e.g. at least 0.5 or at least 1, this indicates overexpression of the according biomarker RNA molecule. If the $\Delta Ct$ is 0 or below, this indicates that the according biomarker molecule is not overexpressed. In embodiments, a further control is additionally considered in the calculation (e.g. to detect contaminations, such as a leukocyte contamination, e.g. based on CD45 expression), e.g. by determining a $\Delta\Delta Ct$. The $\Delta\Delta Ct$ can be determined according to the following principle: $\Delta\Delta Ct = (CutOff_{(gene)} - SampleCt_{(gene)}) - (CutOff_{(control)} - SampleCt_{(control)})$.

According to one embodiment, determining the expression of at least one biomarker RNA molecule in the isolated RNA in step (A) and/or step (B) comprises performing one or more control reactions to detect or consider potential contaminations. As is explained in the example section, e.g. a common contamination in isolated CTCs from blood results from leukocytes. Expression of the biomarker RNA molecules in leukocytes can influence the expression results. Therefore, it is advantageous to perform one or more control reactions to determine an according contamination in CTCs, and/or EVs, optionally CTCs and EVs. The results can then be considered and thus included in the determination of the expression of the RNA biomarker molecule. Suitable methods for taking such potential contaminations into account are known in the art and exemplary methods are also described in the examples. According to one embodiment, expression of an according control gene such as e.g. CD45 is considered in the determination of the expression of the biomarker RNA molecule, e.g. by determining in a qPCR the $\Delta\Delta VCt = (CutOff_{(gene)} - SampleCt_{(gene)}) - CutOff_{(CD45)} - SampleCt_{(CD45)})$.

Where it is referred herein to that the expression level of a certain biomarker RNA molecule or biomarker RNA combination in CTCs and/or EVs is indicative for a certain medical or diagnostic finding, it is self-evident that the expression of such biomarker RNA molecule or biomarker combination is, respectively has been determined in step (A) and/or (B).

Biological Samples Comprising Circulating Tumor Cells and Extracellular Vesicles As discussed herein, the present method can be performed as in vitro method using a biological sample that has been obtained from a subject, e.g. a cancer patient. The biological sample comprises or is suspected or comprising circulating tumor cells and extracellular vesicles such as in particular exosomes. Suitable biological samples known to comprise circulating tumor cells and extracellular vesicles are well known in the art and therefore, need no detailed description herein.

Preferably, the biological sample is a liquid sample, such as a liquid biopsy sample. The advantages of liquid biopsy samples are well-known. They can be easily obtained by minimal invasive methods, such as e.g. blood draw. This also simplifies the repeated analysis.

According to one embodiment, the biological sample is a bodily fluid. In one embodiment the biological sample is selected from blood, urine, peritoneal effusions and pleural effusions, bone marrow aspirates and nipple aspirates. The biological sample is preferably selected from blood and urine. In one embodiment, the biological sample is blood, in particular peripheral blood. As is demonstrated by the examples, circulating tumor cells and extracellular vesicles such as exosomes can be easily isolated from blood samples and analysed with the present methods. Suitable methods for processing an according biological sample such as a blood sample were also described above and it is referred to the above disclosure. The described workflows enable expression profiling in CTCs as well as in extracellular vesicles comprised in according biological samples.

Subjects

As discussed above, a biological sample can be obtained from a subject and the method according to the present invention can be performed as in vitro method using the biological sample. Exemplary suitable and preferred embodiments for biological samples and workflows for the analysis are discussed above and it is referred to the corresponding disclosure.

In one embodiment, the subject is a human subject. As discussed above, the method according to the present invention can be advantageously used as diagnostic, prognostic and/or predictive aid in the management of patients, in particular cancer patients. According to one embodiment, the subject is afflicted or suspected of being afflicted with a disease, in particular cancer. In one embodiment, the patient is afflicted or suspected of being afflicted with a solid cancer such as breast cancer. In one embodiment, the patient is afflicted or suspected of being afflicted with a metastatic solid cancer. Metastases include but are not limited to bone metastases, visceral metastases, lymphoid metastases and brain metastases. In one embodiment, the patient is afflicted or suspected of being afflicted with breast cancer, in particular metastatic breast cancer. According to one embodiment, the primary breast cancer tumor is HER2− or HER2+. According to one embodiment, the primary breast tumor is HER2−. According to one embodiment the metastatic breast cancer patient has or is at risk of developing bone metastases.

As is also demonstrated by the examples, the present method is particularly useful for the analysis of breast cancer patients, in particular patients afflicted or suspected of being afflicted with metastatic breast cancer. The findings and preferred embodiments described herein therefore particularly apply to breast cancer patients, in particular metastatic breast cancer patients. However, the present method can also be applied to and is advantageous with respect to other cancer patients. E.g. the informative value of CTCs is not only established in breast cancer, but also in numerous other solid cancers including but not limited to prostate cancer, colon cancer, lung cancer and other. Extracellular vesicles such as exosomes play as part of the tumor microenvironment an important role e.g. in fibroblast growth, desmoplastic reactions but also initiation of EMT and SC as well as therapy resistance building and initiation of metastases. This is relevant for numerous solid cancers.

The present method which considers in a combined analysis the results from the CTC expression profile and the results from the EV expression profile, e.g. by providing a combined expression profile, therefore improves the significance and thus the value of the obtained diagnostic, prognostic and/or predictive information for solid cancers in general. Accordingly, in one embodiment the subject is a patient afflicted or suspected of being afflicted with a solid cancer selected from breast cancer, prostate cancer, colon cancer, lung cancer, ovarian cancer, bladder cancer, pancreatic cancer, gastric cancer, liver cancer, sarcoma and melanoma. As discussed above, the cancer can be a metastatic cancer.

Biomarker RNA Molecules

Circulating biomarker RNA molecules are of high value. The biomarkers are analyzed herein based on RNA expression and therefore, are referred to herein as biomarker RNA molecules. As is explained herein, biomarker RNA molecules analyzed in the present method are often transcripts of tumor associated genes (see e.g. Table I for according genes).

The one or more biomarker RNA molecules analysed in step (A) and step (B) can be selected from protein-coding or non-protein coding RNAs and preferably are selected from mRNA and miRNA. As discussed herein, it is preferred to analyse the expression of two or more biomarker RNA molecules, preferably a marker panel, in step (A) and/or step (B), more preferably step (A) and step (B).

It is established in the art that mRNA transcripts of marker genes provide valuable molecular information. Accordingly, in one embodiment, the at least one biomarker RNA molecule analysed in step (A) and/or step (B) is a mRNA. Suitable and preferred embodiments are discussed herein. The one or more biomarker mRNAs analyzed in the present method can represent transcripts of tumor-associated genes. According genes are e.g. listed in Table I. (FIG. 5) and the expression of transcripts of according genes can be analysed as biomarker RNA molecules in conjunction with the present method. Further transcripts of marker genes and according mRNAs suitable as biomarker RNA are also known in the art and can be identified by the skilled person without undue burden. According mRNA transcripts can thus also be used as biomarker RNA molecule in the present method. According to one embodiment, all biomarker RNA molecules analysed in step (A) and step (B) are mRNA transcripts. According to one embodiment, mRNA and miRNA are used, respectively are analysed as biomarker RNA molecules in step (A) and step (B).

According to one embodiment, the biomarker RNA molecule is a miRNA. It is known in the art that miRNAs can also provide valuable molecular information. E.g. signatures of miRNAs were found to be characteristic of tumor type and developmental origin. MiRNAs have been already associated with EVs. Accordingly, in one embodiment, the at least one biomarker RNA molecule analysed in step (A) and/or step (B) is a miRNA. Suitable embodiments for biomarker miRNAs are known in the art and can also be identified by the skilled person. According to one embodiment, all biomarker RNA molecules analysed in step (A) and step (B) are miRNAs.

According to one embodiment, the at least one biomarker RNA molecule is a cancer-associated tumor marker. As discussed also in detail below, a biomarker RNA molecule can in embodiments be a negative or a positive response marker, e.g. also depending on its expression in CTCs and/or EVs.

According to one embodiment, the at least one biomarker RNA molecule is a diagnostic, prognostic and/or predictive biomarker. Preferably, the at least one biomarker RNA molecule is a prognostic or predictive biomarker. Specifically, the one or more biomarker RNA molecules can be a biomarker associated with or being of potential relevance for the type of cancer the subject is afflicted with. In a preferred embodiment, the biomarker RNA molecule is a diagnostic, prognostic and/or predictive biomarker for breast cancer, in particular for metastatic breast cancer.

As discussed herein, it is preferred to analyse the expression of multiple biomarker RNA molecules, in step (A) and/or step (B), preferably in step (A) and in step (B). Accordingly, a biomarker panel can be analysed in step (A) and/or step (B). According to one embodiment, an according biomarker panel that is analyzed in the present method may comprise 2 to 50, 5 to 100, 10 to 200, 20 to 250, 25 to 300 or 50 to 500 different biomarker RNA molecules. Suitable and preferred biomarker RNA molecules that can be analyzed with the present method are described herein. An according biomarker panel analyzed in the present method may comprise one or more biomarkers selected from the biomarkers shown in Table I. As discussed, Table I. lists inter alia tumor-associated marker genes and the RNA expression level of according genes can be analysed as biomarker RNA molecules in the present method. Hence, according to one embodiment, the at least one RNA biomarker molecule analysed in step (A) and/or step (B), preferably step (A) and (B), is selected from transcripts of genes listed in Table I. According to one embodiment, the expression of an according biomarker panel is analyzed in the present method which comprises at least 2, at least 3, at least 5, at least 7, at least 10, at least 15 or at least 20 biomarkers as shown in Table I. According to one embodiment, an according biomarker panel is analysed in step (A) and step (B).

Expression of the multiple biomarker RNAs (e.g. the biomarker panel) can be analysed in each step (A) and (B), e.g. in parallel or in a multiplex assay to determine the expression results for providing the CTC expression profile and the EV expression profile.

According to one embodiment, the at least one RNA biomarker molecule analysed in step (A) and/or step (B) is selected from the group consisting of (i) transcripts of genes for an epithelial like phenotype, (ii) transcripts of genes for a basal-like phenotype, (iii) transcripts of genes for tyrosine kinase receptors, (iv) transcripts of genes for factors related to therapy resistance, (v) transcripts of genes for factors related to epithelial to mesenchymal transition or tumor stem cells, (vi) transcripts of genes for factors involved in the steroid receptor pathway and (vii) transcripts of genes for factors involved in immune modulation. According genes are known in the art. Table I. lists exemplary embodiments for genes for each class that can be used in conjunction with the present invention. According to one embodiment, the at least one RNA biomarker molecule analysed in step (A) and/or step (B) is selected from transcripts of genes listed in Table I. Biomarker RNA molecules that were tested in the examples are highlighted in bold. As can be seen, certain biomarkers such as e.g. cMET and EGFR belong to more than one class. According to one embodiment, the expression of one or more biomarker RNA molecules belonging to at least two, at least three, at least 4, at least five or at least six of the aforementioned classes (i) to (vii) is analysed in step (A) and/or in step (B), preferably in step (A) and step (B). According to one embodiment, the expression of one or more biomarker RNA molecules of each aforementioned class (i) to (vii) is analysed in step (A) and/or in step (B), preferably in step (A) and step (B).

According to one embodiment, the at least one RNA biomarker molecule analysed in step (A) and/or step (B), preferably step (A) and step (B), is selected from the group consisting of transcripts of genes for a basal-like phenotype,
transcripts of genes for tyrosine kinase receptors,
transcripts of genes for factors related to therapy resistance and
transcripts of genes for factors related to epithelial to mesenchymal transition or tumor stem cells.

According to one embodiment, the expression of one or more biomarker RNA molecules belonging to at least two, at least three or all four aforementioned classes is analysed in step (A) and/or in step (B), preferably in step (A) and step (B).

According to one embodiment, the at least one RNA biomarker molecule analysed in step (A) and/or step (B) is selected from the group consisting of AKT2, ALK, AR, AURKA, BRCA1, cKIT, cMET, EGFR, ERCC1, HER2, HER3, KRT5, mTOR, NOTCH1, PARP1, PI3K and SRC1. The abbreviations are explained in Table I (these markers are listed in bold). According to one embodiment, the expression of at least two, at least three, at least five, at least seven, at least 10, at least 12, at least 15 or of all of the aforementioned biomarker RNA molecules is analysed in step (A) and/or in step (B), preferably in step (A) and step (B).

According to one embodiment, the at least one RNA biomarker molecule is selected from the group consisting of HER2, HER3, cKIT, cMET, AURKA, mTOR and ERCC1. According to one embodiment, the expression of at least two, at least three, at least four, at least five, at least six or of all seven of the aforementioned biomarker RNA molecules is analysed in step (A) and/or in step (B), preferably in step (A) and step (B).

According to one embodiment, the at least one RNA biomarker molecule analysed in step (A) and/or step (B) is selected from the group consisting of HER2, HER3, cKIT, cMET, AURKA and mTOR. According to one embodiment, at least HER2 and/or HER3 is analyzed as at least one biomarker RNA molecule. According to one embodiment, at least AURKA is analyzed as at least one biomarker RNA molecule. According to one embodiment, at least mTOR is analyzed as at least one biomarker RNA molecule. Advantages of the aforementioned embodiments are described below and in the examples. According to one embodiment, the expression of at least two, at least three, at least four, at least five or of all six of the aforementioned biomarker RNA molecules is analysed in step (A) and/or in step (B), preferably in step (A) and step (B).

According to one embodiment at least the expression of the RNA biomarker molecules HER2 and HER3 is determined in step (A) and step (B). According to one embodiment at least the expression of the RNA biomarker molecules HER2, HER3, cMET and cKIT is determined in step (A) and step (B). According to one embodiment at least the expression of the RNA biomarker molecules HER2, HER3, cMET, cKIT and AURKA is determined in step (A) and step (B). According to one embodiment at least the expression of the RNA biomarker molecules HER2, HER3, cMET, cKIT, AURKA and mTOR is determined in step (A) and step (B).

According to one embodiment at least the expression of the RNA biomarker molecules HER2, HER3, cKIT, cMET, AURKA, mTOR and ERCC1 is determined in step (A) and step (B).

As is demonstrated in the examples, the combined analysis of the CTC and EV expression profiles comprising the results of the aforementioned biomarker RNA molecules and biomarker RNA combinations provides valuable diagnostic, prognostic and/or predictive information that is useful in the management of cancer patients, in particular breast cancer patients such as metastatic breast cancer patients. The correlation between the biomarker RNA expression in CTCs and/or EVs and the therapy response that has been found based on the combined analysis of the CTC and the EV expression profiles is described in further detail herein and it is referred to the respective disclosure.

Generation of the CTC, EV and Combined Expression Profile

As is demonstrated in the examples, the expression profiles of CTCs and EVs showed great differences. The frequencies of positive signals corresponding to an overexpression of an analysed biomarker RNA molecule differed in EVs and CTCs and moreover, inverse correlations to therapy response was observed for specific biomarker RNA molecules (such as e.g. mTOR), depending on whether overexpression was detected in CTCs or EVs. Therefore, the combined analysis of the expression profiles obtained for CTCs and EVs as taught herein significantly improves inter alia the predictive and prognostic value of the obtained results. Depending on the focus of the performed prognostic or predictive analysis and/or the cancer type, the analysis of different biomarker RNA molecules, respectively biomarker panels, can be of interest. Moreover, different expression profiles can be of importance. Therefore, exemplary suitable and preferred examples for generating and thus providing the CTC expression profile, the EV expression profile and moreover the combined expression profile are described in the following.

According to one embodiment, the expression of at least one identical biomarker RNA molecule is determined in step (A) and step (B). E.g. whether said biomarker RNA molecule is overexpressed in CTCs, EVs or both can then be considered in the combined analysis of the results. As discussed above, a combined expression profile can be provided using the expression profiles determined in step (A) and step (B). As discussed above, it is preferred to determine the expression of two or more identical biomarker RNA molecules in steps (A) and step (B). Suitable and preferred embodiments for the number of biomarker RNA molecules to be analyzed as well as suitable and preferred specific biomarker RNA molecules have been described above and it is referred to the respective disclosure. According to one embodiment, the expression of the same biomarker RNA molecules is determined in step (A) and step (B).

According to one embodiment, the method encompasses determining the expression of at least one diverging biomarker RNA molecule in step (A) and step (B). Therefore, the present method also encompasses embodiments, wherein a certain biomarker RNA molecule is analysed in step (A) but not in step (B) or vice versa. This can be feasible, if e.g. a certain biomarker RNA molecule is only of significance if it is overexpressed in CTCs but is not significant if it is expressed in EVs (or vice versa).

According to one embodiment, the expression profile provided in step (A) and/or step (B), preferably steps (A) and (B), comprises the results of analysed biomarker RNA molecules that are determined to be overexpressed. As is demonstrated by the examples, the overexpression of biomarker RNA molecules in CTCs and/or EVs was often found to significantly correlate to therapy response. Therefore, it is advantageous to at least include the results of analysed biomarker RNA molecules that are determined to be overexpressed. Thus, according to one embodiment, the expression profile provided in step (A) and/or step (B) only comprises the results of analysed RNA biomarkers that are determined to be overexpressed and the results for analysed RNA biomarkers that are not overexpressed are not included. According to an alternative embodiment, the expression profile provided in step (A) and/or step (B) comprises results of analysed RNA biomarkers that are determined to be overexpressed and additionally comprises results of analysed RNA biomarkers that are not determined to be overexpressed. As is demonstrated by the present examples, the finding that a certain biomarker RNA molecule is not overexpressed in CTCs and/or EVs can also significantly correlate to therapy response and therefore may also be of predictive or prognostic value. It is thus advantageous to at least include the result that a respective biomarker RNA molecule is not overexpressed in CTCs and/or EVs in the provided expression profiles. According to one embodiment, the expression profile provided in step (A) and/or step (B) comprises the expression results for all biomarker RNA molecules analysed in step (A) and/or step (B), i.e. it comprises the positive (overexpressed) as well as the negative (not overexpressed) expression results. Preferably, the expression profile provided in step (A) and step (B) comprises the expression results for all biomarker RNA molecules analysed in step (A) and step (B).

According to one embodiment, step (C) comprises using from the expression profiles determined in step (A) and/or determined in step (B) results of RNA biomarkers determined to be overexpressed for the combined analysis of the results. According to one embodiment, step (C) comprises using from the expression profile determined in step (A) and/or determined in step (B) results of RNA biomarkers determined to be overexpressed for providing the combined expression profile. According to one embodiment, the combined expression profile provided in step (C) only comprises the results of analysed RNA biomarkers that are determined in step (A) and/or step (B) to be overexpressed and the results for analysed RNA biomarkers that are not overexpressed are not included in the combined expression profile. This embodiment can be feasible if the combined expression profile is provided based on biomarker RNA molecules that are only significant if overexpressed in CTCs and/or EVs. According to an alternative embodiment, step (C) comprises using from the expression profile determined in step (A) and/or determined in step (B) results of analysed RNA biomarkers determined to be overexpressed and additionally results of analysed RNA biomarkers that are not determined to be overexpressed in step (A) and/or step (B) for the combined analysis of the results, respectively to provide the combined expression profile. As is demonstrated by the present examples and as explained before, the finding that a certain biomarker RNA molecule is not overexpressed in CTCs and/or EVs can also significantly correlate to therapy response and therefore is also of predictive or prognostic value. This is particularly the case where the overexpression of a certain biomarker in CTCs has a different meaning compared to when the same biomarker is overexpressed in EVs. This is demonstrated in the examples based on the biomarker RNA molecule for mTOR. Overexpression of mTOR in CTCs but not EVs is significantly correlated to overall-responders, while overexpression of mTOR in EVs but not CTCs is significantly correlated to overall non-responders and thus therapy failure. Thus, the same transcript showed an inverse correlation to therapy response depending on whether said biomarker RNA was expressed in CTCs or EVs. Using the provided CTC and EV expression profiles for a combined analysis additionally taking into account the results that such biomarkers are not overexpressed in CTCs and/or EVs, is in embodiments therefore advantageous. In embodiments, it is therefore advantageous and preferred to include in the combined analysis and hence, in the combined expression profile, the result that an according biomarker RNA molecule is not overexpressed in CTCs and/or EVs. According to one embodiment, step (C) comprises using from the expression profile determined in step (A) and/or determined in step (B), preferably step (A) and step (B), the results for all biomarker RNA molecules analysed in step (A) and/or step (B), preferably step (A) and (B), that are determined to be indicative as response marker for the combined analysis of the results, respectively the generation of the combined expression profile.

According to one embodiment, step (C) comprises using from the expression profiles determined in step (A) and/or determined in step (B) results for all biomarker RNA molecules analysed in step (A) and/or step (B) for the combined analysis of the results, respectively the generation of the combined expression profile. Preferably, step (C) comprises using from the expression profiles determined in step (A) and determined in step (B) results for all biomarker RNA molecules analysed in step (A) and step (B) for the combined analysis of the results, respectively the generation of the combined expression profile.

Moreover, the result that a certain biomarker RNA molecule is down-regulated in CTCs and/or EVs can also be included—if determined—in the expression profile provided in step (A) and/or the expression profile provided in step (B). According results can also be used for the combined analysis in step (C) or for providing the combined expression profile.

Inter Alia Diagnosis, Prognosis, Staging and Monitoring Cancer Patients

The information that is provided based on the combined analysis as taught herein can be used to support the diagnosis, prognosis or to choose the most appropriate treatment for cancer patients. Details of the cancer patients were already described above and it is referred to the above disclosure which also applies here. Subsequently, suitable and preferred embodiments are described how the present method can be used as diagnostic, prognostic and/or predictive aid in the management of cancer patients. This disclosure in particular applies to subjects with breast cancer, in particular metastatic breast cancer. Where it is discussed that the expression level of a certain biomarker RNA molecule or biomarker RNA combination in CTCs and/or EVs is indicative for a certain medical or diagnostic finding, it is self-evident that the expression of such biomarker RNA molecule or biomarker combination is, respectively has been determined in step (A) and/or (B), as will result from the presented context.

According to one embodiment, the method further comprises using the results of the combined analysis for medical prognosis, diagnosis and/or treatment choice. As discussed above, the combined analysis in step (C) preferably comprises providing a combined expression profile using the CTC expression profile provided in (A) and the EV expression profile provided in (B). Accordingly, in one embodiment the method comprises using the combined expression profile for medical prognosis, diagnosis and/or treatment choice. The present method may further comprise providing a medical prognosis and/or diagnosis based on the combined expression profile.

According to one embodiment, the method further comprises using the results of the combined analysis for predicting or monitoring response to therapy. According to one embodiment, the method further comprises using the combined expression profile for predicting or monitoring response to therapy.

According to one embodiment, the patient is predicted to respond to or is predicted not to respond to therapy based on the results of the combined analysis. According to one embodiment, the patient is predicted to respond, or is predicted not to respond to therapy based on the combined expression profile. The present method may also include changing the therapy based on the results of the combined analysis, e.g. by administering another therapeutic agent either instead of or in addition to the existing therapy.

Cancer Therapy

According to one embodiment, the present method is a method of determining the effectiveness of a therapy administered to a human subject afflicted with cancer. Accordingly, therapy preferably is cancer therapy. The cancer therapy may be selected from chemotherapy, hormone therapy, targeted therapy, immunotherapy, therapy with angiogenesis inhibitors and radiotherapy. Targeted cancer therapy may involve the use of a therapeutic agent specifically targeting the cancer. Examples of targeted therapeutic agents include but are not limited to therapeutic binding agents such as therapeutic antibodies and functional fragments thereof specifically targeting the cancer by binding e.g. HER2, EGFR or mTOR or corresponding kinase inhibitors, which can be small molecules. Targeted therapeutic agents include e.g. therapeutic agents that target HER2 (e.g. anti-HER2 antibodies such as trastuzumab and HER2 kinase inhibitors such as lapatinib), EGFR (e.g. anti-EGFR antibodies such as Cetuximab and EGFR inhibitors such as gefitinib) or mTOR (e.g. mTOR inhibitors such as everolimus). Furthermore, the therapy can target the cancer environment, by targeting e.g. bones (e.g. bone stabilization therapy using e.g. therapeutic antibodies like denosumab or bisphonsphonates), vascularization (e.g. angiogenesis inhibitors such as bevacizumab) and immunotherapy (e.g. anti-PD-L1 immunotherapy). Details of the cancer patients were already described above and it is referred to the above disclosure which also applies here.

According to one embodiment, the cancer therapy comprises treatment with a therapeutic antibody. In one embodiment, the therapeutic antibody is a targeted antibody. In one embodiment, the therapeutic antibody is an anti-RANKL-antibody, preferably denosumab.

According to one embodiment, the cancer therapy comprises a bone stabilization therapy. Bone stabilization therapy is frequently used in cancer therapy of solid cancers such as breast cancer, to prevent or treat bone metastasis. According to one embodiment, the bone stabilization therapy comprises treatment with an anti-RANKL-antibody and/or bisphosphonates. The anti-RANKL antibody may be denosumab. Any disclosure provided herein relating to bone stabilization therapy, in particular applies to a therapy with an anti-RANKL-antibody such as denosumab, specifically.

As is demonstrated by the examples, the present invention can be advantageously used for predicting response to cancer therapy, in particular chemotherapy and bone stabilization therapy, based on the combined analysis of the CTC and EV expression profiles.

Use of the Results of the Present Method

According to one embodiment, the method further comprises using the results of the combined analysis, preferably the combined expression profile, for classifying the subject based on the expression profiles determined in (A) and (B). Optionally, classifying comprises assigning the subject to one or more of the following classes:

Response to therapy, such as response to targeted therapy, chemotherapy, hormone therapy and/or radiation therapy;

Failure of therapy, such as failure of targeted therapy, chemotherapy, hormone therapy and/or radiation therapy;

Disease-free survival;

Overall-survival;

Re-evaluation prognosis;

Qualification for companion diagnostics (cDx); and/or

Stratification for drug development.

According to one embodiment, the method further comprises using the results of the combined analysis, preferably the combined expression profile, for predicting or detecting cancer progression. The present method can be used as aid to detect or predict the development of metastases.

Moreover, the present method can be used as aid to detect or predict the development of metastases having a different status than the primary tumor. E.g. if a cancer associated tumor marker (e.g. HER2) is not expressed in the primary tumor (e.g. status: HER2−) as is reflected in the EV expression profile, wherein the respective biomarker RNA (e.g. HER2) is determined as not being expressed (or as not being overexpressed), but is determined to be overexpressed CTCs and is included in the CTC expression profile, the combined analysis of the CTC expression profile and the EV expression profile is indicative that metastases deriving from such CTCs will have a different status (e.g. HER2+) than the primary tumor. Accordingly, this is an indicator that the metastases require a different therapy than the primary tumor (e.g. HER2 targeted therapy). According to one embodiment, the method further comprises administering to the patient an appropriate targeted therapy based on the expression result obtained for the CTCs (e.g. HER2 targeted therapy, if the CTCs are determined HER2 positive, while the EVs are HER2 negative). Accordingly, the present invention, which uses the expression profiles of CTCs and EVs for a combined analysis of the results, is particularly advantageous. It allows the early detection of such metastasizing mechanisms which, if remaining undetected, can be detrimental for the patient.

According to one embodiment, the method further comprises using the results of the combined analysis, preferably the combined expression profile, for therapy stratification.

According to one embodiment, the method comprises performing steps (A) to (C) at different time points and comparing the results. Determining the expression profile of the analyzed one or more biomarker RNA molecules in circulating tumor cells and EVs and using the determined CTC and EV expression profiles for a combined analysis of the results, e.g. by providing a combined expression profile, at a second time point is done by the method according to the invention. The present method can be performed repeatedly at a second, third, fourth, fifth, sixth or multiple different time points. In each case, the results of the combined analysis, such as the combined expression profile, provided for a given time point can be compared with one another. Comparing e.g. the combined expression profiles obtained for at least one, at least two or at least three different time points is advantageous e.g. for monitoring a response to therapy or of disease progression.

Also provided are corresponding methods for the diagnosis, prognosis, staging, and monitoring of cancer patients based on the combined analysis performed with the method according to the first aspect. Corresponding methods accordingly comprise performing the method according to the first aspect. Also provided are methods for monitoring the progression of cancer, determining the efficacy of a therapeutic agent or determining a targeted therapy for cancer patients which comprise performing the method according to the first aspect.

Correlations of the Expression Profiles to Therapy Response

As is demonstrated in the examples, the overexpression of certain biomarker RNA molecules in CTCs and/or EVs or the absence thereof can be indicative of either a positive or negative response to therapy (e.g. therapy success or failure), often further depending on whether the biomarker RNA molecules are detected in CTCs or EVs. Similar considerations apply in embodiments to biomarker RNA molecules that are not expressed, respectively not overexpressed in CTCs and/or EVs. The present method, which uses the CTC and EV expression profiles for a combined analysis of the results, e.g. by providing a combined expression profile, takes these important factors into account, thereby significantly improving the value of the obtained results. Subsequently, important correlations to therapy response observed are outlined in general. These correlations to therapy response are then further explained in conjunction with specific biomarkers where such correlations were found in the performed examples. Where it is disclosed that the expression level of a certain biomarker RNA molecule or biomarker RNA combination in CTCs and/or EVs is indicative for a certain medical or diagnostic finding as described in further detail below, it is self-evident that the expression level of such biomarker RNA molecule or biomarker combination is, respectively has been, determined in step (A) and/or (B), as will result from the presented context.

Other biomarkers will demonstrate correlations according to the same basic patterns described herein, wherein the specific biomarker RNA molecules and their expression levels may differ e.g. depending on the cancer type and the administered therapy. The present method is an important tool for identifying and using such correlations that are identified by a combined analysis of the expression profiles obtained for CTCs and EVs.

General Correlation Pattern: Overexpression of at Least One Biomarker RNA Molecule in CTCs and/or EVs is Related to a Negative Response to Therapy A biomarker RNA molecule expressed in CTCs and/or EVs can be a negative response marker. E.g. if overexpression of such biomarker RNA molecule is determined in CTCs and/or EVs, this can be indicative for a negative response to therapy. This is demonstrated in the examples. Subsequently, examples are provided showing how such a finding can correlate with a negative response to therapy.

According to one embodiment, identifying in the combined analysis, preferably the combined expression profile, overexpression of the at least one biomarker RNA molecule in circulating tumor cells and/or extracellular vesicles is indicative of disease progression. According to one embodiment, identifying in the combined analysis, preferably the combined expression profile, overexpression of the at least one biomarker RNA molecule in circulating tumor cells and/or extracellular vesicles is indicative of therapy failure or resistance to therapy. According to one embodiment, identifying in the combined analysis, preferably the combined expression profile, overexpression of the at least one biomarker RNA molecule in circulating tumor cells and/or extracellular vesicles is indicative that the therapeutic agent is ineffective, respectively that the subject is not benefitting from the therapy.

As is demonstrated in the examples, the analysed biomarkers may also have a different significance as negative response marker depending on whether they are expressed in CTCs or EVs, respectively the detected expression level in CTCs or EVs. The present method, which is based on a combined analysis of the expression profiles obtained for CTCs and EVs, allows taking these factors into account.

Certain biomarker RNA molecules are particularly relevant as negative response marker, if expressed, in particular overexpressed, in CTCs. Accordingly, in one embodiment, identifying in the combined analysis, preferably the combined expression profile, overexpression of the at least one biomarker RNA molecule in circulating tumor cells and optionally extracellular vesicles is indicative of disease progression and/or therapy failure or resistance to therapy. Identifying in the combined analysis, preferably the combined expression profile, overexpression of the at least one biomarker RNA molecule in circulating tumor cells and optionally extracellular vesicles can thus be indicative that the therapeutic agent is ineffective, respectively that the subject is not benefitting from the therapy.

Certain biomarker RNA molecules are particularly relevant as negative response marker, if expressed, in particular overexpressed, in EVs. Accordingly, in one embodiment identifying in the combined analysis, preferably the combined expression profile, overexpression of the at least one biomarker RNA molecule in extracellular vesicles and optionally circulating tumor cells is indicative of disease progression and/or therapy failure or resistance to therapy. Identifying in the combined analysis, preferably the combined expression profile, overexpression of the at least one biomarker RNA molecule in extracellular vesicles and optionally circulating tumor cells is indicative that the therapeutic agent is ineffective, respectively that the subject is not benefitting from the therapy.

Moreover, certain biomarker RNA molecules are particularly relevant as negative response marker, if expressed, in particular overexpressed, in EVs but not in CTCs (see e.g. mTOR in the examples). Accordingly, in one embodiment, identifying in the combined analysis, preferably the combined expression profile, overexpression of the at least one biomarker RNA molecule in extracellular vesicles but not in circulating tumor cells is indicative of disease progression and/or therapy failure or resistance to therapy. Identifying in the combined analysis, preferably the combined expression profile, overexpression of the at least one biomarker RNA molecule in extracellular vesicles but not in circulating tumor cells is indicative that the therapeutic agent is ineffective, respectively that the subject is not benefitting from the therapy.

According to another embodiment, identifying in the combined analysis, preferably the combined expression profile, overexpression of the at least one biomarker RNA molecule in circulating tumor cells but not in extracellular vesicles is indicative of disease progression and/or therapy failure or resistance to therapy. In one embodiment, identifying in the combined analysis, preferably the combined expression profile, overexpression of the at least one biomarker RNA molecule in circulating tumor cells but not in extracellular vesicles is indicative that the therapeutic agent is ineffective, respectively that the subject is not benefitting from the therapy.

The present method which is based on the combined analysis of the results of the CTC and EV expression profiles advantageously allows to consider these correlation patterns of different negative response markers in combination, thereby improving the obtained results. This is of particular value when analyzing the expression of several biomarker RNA molecules.

Details regarding the subject, particular cancer types and examples of cancer therapies are discussed in detail above and the disclosure also applies here.

General Correlation Pattern: Overexpression of at Least One Biomarker RNA Molecule in CTCs and/or EVs is Related to a Positive Response to Therapy A biomarker RNA molecule expressed in CTCs and/or EVs can also be a positive response marker. E.g. if overexpression of such a biomarker RNA molecule is determined in CTCs and/or EVs, this can be indicative for a positive response to therapy. This is also demonstrated in the examples. Subsequently, examples are provided showing how such a finding can correlate with a positive response to therapy.

According to one embodiment, identifying in the combined analysis, preferably the combined expression profile, overexpression of the at least one biomarker RNA molecule in circulating tumor cells and/or extracellular vesicles is indicative of progression-free survival. According to one embodiment, identifying in the combined analysis, preferably the combined expression profile, overexpression of the at least one biomarker RNA molecule in circulating tumor cells and/or extracellular vesicles is indicative of therapy response, respectively that the subject is benefitting from the therapy. "Therapy response" as used herein includes stable disease and tumor regression.

As is demonstrated in the examples, the analysed biomarkers may also have a different significance as positive response marker depending on whether they are expressed, in particular overexpressed in CTCs or EVs. The present method, which is based on a combined analysis of the expression profiles obtained for CTCs and EVs allows to take these factors into account.

Certain biomarker RNA molecules are particularly relevant as positive response marker, if expressed, in particular overexpressed, in CTCs. Accordingly, in one embodiment, identifying in the combined analysis, preferably the combined expression profile, overexpression of the at least one biomarker RNA molecule in circulating tumor cells and optionally extracellular vesicles is indicative of progression-free survival. According to one embodiment, identifying in the combined analysis, preferably the combined expression profile, overexpression of the at least one biomarker RNA molecule in circulating tumor cells and optionally extracellular vesicles is indicative of therapy response, respectively that the subject is benefitting from the therapy.

Certain biomarker RNA molecules are particularly relevant as positive response marker, if expressed, in particular overexpressed, in EVs. Accordingly, in one embodiment identifying in the combined analysis, preferably the combined expression profile, overexpression of the at least one biomarker RNA molecule in extracellular vesicles and optionally circulating tumor cells is indicative of progression-free survival. According to one embodiment, identifying in the combined analysis, preferably the combined expression profile, overexpression of the at least one biomarker RNA molecule in extracellular vesicles and optionally circulating tumor cells is indicative of therapy response, respectively that the subject is benefitting from the therapy.

Moreover, certain biomarker RNA molecules are particularly relevant as positive response marker, if expressed, in particular overexpressed in CTCs but not in EVs (see e.g. mTOR in the examples). Accordingly, in one embodiment identifying in the combined analysis, preferably the combined expression profile, overexpression of the at least one biomarker RNA molecule in circulating tumor cells but not in extracellular vesicles is indicative of progression-free survival. According to one embodiment, identifying in the combined analysis, preferably the combined expression profile, overexpression of the at least one biomarker RNA molecule in circulating tumor cells but not extracellular vesicles is indicative of therapy response, respectively that the subject is benefitting from the therapy.

According to another embodiment, identifying in the combined analysis, preferably the combined expression profile, overexpression of the at least one biomarker RNA molecule in extracellular vesicles but not circulating tumor cells is indicative of progression-free survival. According to one embodiment, identifying in the combined analysis, preferably the combined expression profile, overexpression of the at least one biomarker RNA molecule in extracellular vesicles but not in circulating tumor cells is indicative of therapy response, respectively that the subject is benefitting from the therapy.

The present method which is based on the combined analysis of the results of the CTC and EV expression profiles advantageously allows to consider these correlation patterns of different positive response markers in combination, thereby improving the obtained results. This is of particular value when analyzing several biomarker RNA molecules.

Details regarding the subject, particular cancer types and examples of cancer therapies are discussed in detail above and the disclosure also applies here.

General Correlation Pattern: No Overexpression of at Least One Biomarker RNA Molecule in CTCs and/or EVs is Related to a Positive Response to Therapy Furthermore, biomarker RNA molecules can also represent a positive response marker, if they are not overexpressed in CTCs and/or EVs, wherein no overexpression also includes the absence of expression. E.g. if expression of such a biomarker RNA molecule is not determined in CTCs and/or EVs, this can be indicative for a positive response to therapy. This is also demonstrated in the examples. Subsequently, examples are provided illustrating how such a finding can correlate with a positive response to therapy.

According to one embodiment, identifying in the combined analysis, preferably the combined expression profile, that the at least one biomarker RNA molecule is not overexpressed in circulating tumor cells and/or extracellular vesicles is indicative of progression-free survival. According to one embodiment, identifying in the combined analysis, preferably the combined expression profile, that the at least one biomarker RNA molecule is not overexpressed in circulating tumor cells and/or extracellular vesicles is indicative of therapy response, respectively that the subject is benefitting from the therapy.

Again, the analysed biomarkers may also have a different significance as positive response marker depending on whether they are not expressed in CTCs or EVs. The present method, which is based on a combined analysis of the expression profiles obtained for CTCs and EVs allows to take these factors into account.

Certain biomarker RNA molecules may be particularly relevant as positive response marker, if they are not expressed in CTCs. Accordingly, in one embodiment, identifying in the combined analysis, preferably the combined expression profile, that the at least one biomarker RNA molecule is not overexpressed in circulating tumor cells and optionally extracellular vesicles is indicative of progression-free survival. According to one embodiment, identifying in the combined analysis, preferably the combined expression profile, that the at least one biomarker RNA molecule is not overexpressed in circulating tumor cells and optionally extracellular vesicles is indicative of therapy response, respectively that the subject is benefitting from the therapy. According to one embodiment, the according biomarker RNA molecule which is not overexpressed in CTCs is expressed in EVs.

Certain biomarker RNA molecules may be particularly relevant as positive response marker, if they are not expressed in EVs. Accordingly, in one embodiment, identifying in the combined analysis, preferably the combined expression profile, that the at least one biomarker RNA molecule is not overexpressed in extracellular vesicles and optionally circulating tumor cells is indicative of progression-free survival. According to one embodiment, identifying in the combined analysis, preferably the combined expression profile, that the at least one biomarker RNA molecule is not overexpressed in extracellular vesicles and optionally circulating tumor cells is indicative of therapy response, respectively that the subject is benefitting from the therapy. According to one embodiment, the according biomarker RNA molecule which is not overexpressed in EVs is expressed in CTCs.

Details regarding the subject, particular cancer types and examples of cancer therapies are discussed in detail above and the disclosure also applies here.

Specific Correlation Pattern: Overexpression of Receptor Tyrosine Kinases as the at Least One Biomarker RNA Molecule in CTCs and/or EVs is Related to a Negative Response to Therapy The examples demonstrate that the expression of receptor tyrosine kinases as biomarker RNA molecule in CTCs and/or EVs represent a negative response marker. The examples demonstrate that if overexpression of such receptor tyrosine kinases as biomarker RNA molecule is determined in CTCs and/or EVs, this was found to be indicative for a negative response to therapy, in particular chemotherapy.

Accordingly, in one embodiment, identifying in the combined analysis, preferably the combined expression profile, overexpression of at least one receptor tyrosine kinase as biomarker RNA molecule in circulating tumor cells and/or extracellular vesicles is indicative of disease progression. According to one embodiment, identifying in the combined analysis, preferably the combined expression profile, overexpression of at least one receptor tyrosine kinase as biomarker RNA molecule in circulating tumor cells and/or extracellular vesicles is indicative of therapy failure or resistance to therapy. According to one embodiment, identifying in the combined analysis, preferably the combined expression profile, overexpression of the at least one receptor tyrosine kinase as biomarker RNA molecule in circulating tumor cells and/or extracellular vesicles is indicative that the therapeutic agent is ineffective, respectively that the subject is not benefitting from the therapy. Preferably, the expression of at least two, at least three or at least four receptor tyrosine kinases is determined in the respective methods. As is demonstrated in the examples, the significance increases with the number of receptor tyrosine kinases considered. According to one embodiment, the receptor tyrosine kinase is selected from HER2, HER3, cKIT and cMET and wherein more preferably, the expression of at least two, at least three or all four of these receptor tyrosine kinases is determined. Suitable biomarker combinations with receptor tyrosine kinases are also described elsewhere herein and it is referred to the respective disclosure.

As is demonstrated in the examples, receptor tyrosine kinases as biomarker RNA molecules are particularly relevant as negative response marker, if expressed in CTCs. Accordingly, in one embodiment identifying in the combined analysis, preferably the combined expression profile, overexpression of at least one receptor tyrosine kinase as biomarker RNA molecule in circulating tumor cells and optionally extracellular vesicles is indicative of disease progression and/or therapy failure or resistance to therapy. It can moreover indicate that the therapeutic agent is ineffective (see above). As discussed above, preferably several receptor tyrosine kinases are analysed. According to one embodiment, the receptor tyrosine kinase is selected from HER2, HER3, cKIT and cMET and wherein preferably, the expression of at least two, at least three or all four receptor tyrosine kinases is determined. Suitable biomarker combinations with receptor tyrosine kinases are also described elsewhere herein and it is referred to the respective disclosure.

As is demonstrated by the examples, the results obtained in CTCs are significant by themselves. However, the results are improved, if the expression of the receptor tyrosine kinases in EVs is additionally taken into account in the combined analysis of the CTC and EV expression profiles according to the invention. As is moreover demonstrated in the examples, the significance increases with the number of receptor tyrosine kinases considered in CTCs and EVs. Thus, the combined evaluation of the combination of several receptor tyrosine kinases, combined in CTCs and EVs, yielded the highest significance.

Details regarding the subject, particular cancer types and examples of cancer therapies are discussed in detail above and the disclosure also applies here. Receptor tyrosine kinases in particular represent a negative response marker in patients with breast cancer, in particular metastatic breast cancer.

According to one embodiment, the therapy is chemotherapy. As is demonstrated in the examples, receptor tyrosine kinases were found to be a negative response marker in relation to chemotherapy. Accordingly, determining in the combined analysis, preferably the combined expression profile, overexpression of the at least one receptor tyrosine kinase as biomarker RNA molecule in circulating tumor cells and/or extracellular vesicles is indicative of chemotherapy failure or resistance to chemotherapy.

According to one embodiment, the method further comprises treating the subject with a different therapeutic agent. E.g. a targeted therapy can be administered in addition to or instead of chemotherapy.

Specific Correlation Pattern: Overexpression of AURKA as the at Least One Biomarker RNA Molecule in CTCs and/or EVs is Related to a Negative Response to Therapy The examples demonstrate that the expression of AURKA as biomarker RNA molecule in CTCs and/or EVs represent a negative response marker. The examples demonstrate that if overexpression of AURKA is determined in EVs and/or CTCs, this was found to be indicative for a negative response to therapy, in particular to a bone stabilization therapy e.g. involving the use of an anti-RANKL antibody such as denosumab. These findings are also relevant for and apply to the second aspect according to the present invention.

Accordingly, in one embodiment, identifying in the combined analysis, preferably the combined expression profile, overexpression of AURKA as at least one biomarker RNA molecule in extracellular vesicles and/or circulating tumor cells is indicative of disease progression. According to one embodiment, identifying in the combined analysis, preferably the combined expression profile, overexpression of AURKA as at least one biomarker RNA molecule in extracellular vesicles and/or circulating tumor cells is indicative of therapy failure or resistance to therapy. According to one embodiment, identifying in the combined analysis, preferably the combined expression profile, overexpression of AURKA as at least one biomarker RNA molecule in extracellular vesicles and/or circulating tumor cells is indicative that the therapeutic agent is ineffective, respectively that the subject is not benefitting from the therapy.

As is demonstrated in the examples, AURKA as biomarker RNA molecule is particularly relevant as negative response marker, if expressed, in particular overexpressed, in EVs. Accordingly, in one embodiment, identifying in the combined analysis, preferably the combined expression profile, overexpression of AURKA as at least one biomarker RNA molecule in extracellular vesicles and optionally circulating tumor cells is indicative of disease progression. According to one embodiment, identifying in the combined analysis, preferably the combined expression profile, overexpression of AURKA as at least one biomarker RNA molecule in extracellular vesicles and optionally circulating tumor cells is indicative of therapy failure or resistance to therapy. According to one embodiment, identifying in the combined analysis, preferably the combined expression profile, overexpression of AURKA as at least one biomarker RNA molecule in extracellular vesicles and optionally circulating tumor cells is indicative that the therapeutic agent is ineffective.

As is demonstrated by the examples, the results obtained in EVs are significant by themselves. However, the results are improved, if the expression results of AURKA in CTCs is additionally taken into account in the combined analysis of the CTC and EV expression profiles according to the invention.

Details regarding the subject, particular cancer types and examples of cancer therapies are discussed in detail above and the disclosure also applies here. Overexpression of AURKA in particular represents a negative response marker in patients with breast cancer, in particular metastatic breast cancer.

According to one embodiment, the therapy is bone stabilization therapy, in particular involving an anti-RANKL antibody such as denosumab. As is demonstrated in the examples, AURKA was found to be a negative response marker in relation to such bone stabilization therapy.

Accordingly, determining in the combined analysis, preferably the combined expression profile, overexpression of AURKA in extracellular vesicles and/or circulating tumor cells is indicative of denosumab therapy failure or resistance to denosumab therapy.

According to one embodiment, the method further comprises treating the subject with a different therapeutic agent.

Specific Correlation Pattern: Overexpression of mTOR as the at Least One Biomarker RNA Molecule in EVs (But Not CTCs) is Related to a Negative Response to Therapy The examples demonstrate that the expression of mTOR as biomarker RNA molecule in EVs (not CTCs) represent a negative response marker. The examples demonstrate that if overexpression of mTOR is determined EVs, this was found to be indicative for a negative response to therapy. In contrast, if mTOR was found to be overexpressed in CTCs (not EVs), mTOR represents a positive response marker (see below). Thus, the same transcript (mTOR) showed an inverse correlation to therapy response depending on whether mTOR expression was detected in EVs or CTCs. This further underscores that the method according to the present invention, which uses the expression profiles determined for EVs and CTCs for a combined analysis of the results is particularly advantageous.

As is demonstrated in the examples, mTOR is relevant as negative response marker, if expressed, respectively overexpressed, in EVs. Accordingly, in one embodiment, identifying in the combined analysis, preferably the combined expression profile, overexpression of mTOR as at least one biomarker RNA molecule in extracellular vesicles, but not in CTCs, is indicative of disease progression. According to one embodiment, identifying in the combined analysis, preferably the combined expression profile, overexpression of mTOR as at least one biomarker RNA molecule in extracellular vesicles, but not in CTCs, is indicative of therapy failure or resistance to therapy.

As is demonstrated in the examples, identifying in the combined analysis, preferably the combined expression profile, overexpression of mTOR as at least one biomarker RNA molecule in extracellular vesicles, but not in CTCs, is indicative that the therapeutic agent is ineffective and accordingly, that the subject is not benefitting from the therapy.

Details regarding the subject, particular cancer types and examples of cancer therapies are discussed in detail above and the disclosure also applies here. Overexpression of mTOR in EVs (but not CTCs) in particular represents a negative response marker in patients with breast cancer, in particular metastatic breast cancer.

Specific Correlation Pattern: Overexpression of Receptor Tyrosine Kinases as the at Least One Biomarker RNA Molecule in CTCs and AURKA in EVs is Related to a Negative Response to Therapy It can be advantageous to consider several negative response markers in the combined analysis of the CTC and EV expression profiles. The above discussed negative response markers may also be considered in combination. Examples are listed in the following.

According to one embodiment, identifying in the combined analysis, preferably the combined expression profile, (i) overexpression of at least one receptor tyrosine kinase as biomarker RNA molecule in circulating tumor cells and (ii) overexpression of AURKA as at least one biomarker RNA molecule in extracellular vesicles is indicative of disease progression. According to one embodiment, identifying in the combined analysis, preferably the combined expression profile, (i) overexpression of at least one receptor tyrosine kinase as biomarker RNA molecule in circulating tumor cells and (ii) overexpression of AURKA as at least one biomarker RNA molecule in extracellular is indicative of therapy failure or resistance to therapy. According to one embodiment, identifying in the combined analysis, preferably the combined expression profile, (i) overexpression of at least one receptor tyrosine kinase as biomarker RNA molecule in circulating tumor cells and (ii) overexpression of AURKA as at least one biomarker RNA molecule in extracellular vesicles is indicative that the therapeutic agent is ineffective, respectively that the subject is not benefitting from the therapy. According to one embodiment, an according finding is indicative of chemotherapy and denosumab failure.

Details regarding the subject, particular cancer types and examples of cancer therapies are also discussed in detail above and the disclosure also applies here. The patient can be afflicted with breast cancer, in particular metastatic breast cancer.

The above methods may additionally determine e.g. the expression of mTOR as further biomarker RNA molecule. As discussed above, if expression of mTOR is detected in EVs (but not CTCs), this is also indicative for a negative response to therapy.

As has been discussed above, preferably, the expression of two or more receptor tyrosine kinases is determined and taken into account in the combined analysis (see above). Preferably, the receptor tyrosine kinase is selected from HER2, HER3, cKIT and cMET. As discussed above, it is preferred that expression of two or more, three or more or more preferably all of these receptor tyrosine kinases is determined and considered in the combined analysis.

Specific Correlation Pattern: Overexpression of ERCC1 as the at Least One Biomarker RNA Molecule in EVs is Related to a Negative Response to Therapy The examples demonstrate that the expression of ERCC1 as biomarker RNA molecule in EVs represents a negative response marker. The examples demonstrate that if overexpression of ERCC1 is determined EVs, this was found to be indicative for a negative response to therapy. Accordingly, in one embodiment, identifying in the combined analysis, preferably the combined expression profile, overexpression of ERCC1 as at least one biomarker RNA molecule in extracellular vesicles is indicative of disease progression and/or therapy failure or resistance to therapy. According to one embodiment, identifying in the combined analysis, preferably the combined expression profile, overexpression of ERCC1 as at least one biomarker RNA molecule in extracellular vesicles indicates that the therapeutic agent is ineffective, respectively that the subject is not benefitting from the therapy.

Details regarding the subject, particular cancer types and examples of cancer therapies are also discussed in detail above and the disclosure also applies here. The subject can be afflicted with breast cancer, in particular metastatic breast cancer.

Further Negative Response Markers

Also the overexpression of further biomarker RNA molecules, such as AR and KRT5, appeared to correlate with a negative response to therapy and therefore, could be useful either alone or in combination with other biomarker RNA molecules (see above) as negative response marker. Accordingly, in one embodiment, identifying in the combined analysis, preferably the combined expression profile, overexpression of AR and/or KRT5 as at least one biomarker RNA molecule in extracellular vesicles is indicative of disease progression. According to one embodiment, identifying in the combined analysis, preferably the combined expression profile, overexpression of AR and/or KRT5 as at least one biomarker RNA molecule in extracellular vesicles is indicative of therapy failure or resistance to therapy. According to one embodiment, identifying in the combined analysis, preferably the combined expression profile, overexpression of AR and/or KRT5 as at least one biomarker RNA molecule in extracellular vesicles indicates that the therapeutic agent is ineffective.

Details regarding the subject, particular cancer types and examples of cancer therapies are also discussed in detail above and the disclosure also applies here. The subject can be afflicted with breast cancer, in particular metastatic breast cancer.

Specific Correlation Pattern: Overexpression of mTOR as at Least One Biomarker RNA Molecule in CTCs (Not EVs) is Related to a Positive Response to Therapy As also discussed elsewhere herein, expression of mTOR in CTCs (not EVs) was identified as positive response marker. The examples demonstrate that if overexpression of mTOR is determined in CTCs (but not EVs) this is indicative for a positive response to therapy.

Accordingly, in one embodiment identifying in the combined analysis, preferably the combined expression profile, overexpression of mTOR as at least one biomarker RNA molecule in circulating tumor cells but not extracellular vesicles is indicative of progression-free survival. According to one embodiment, identifying in the combined analysis, preferably the combined expression profile, overexpression of mTOR as at least one biomarker RNA molecule in circulating tumor cells but not extracellular vesicles, is indicative of therapy response, respectively that the subject is benefitting from the therapy.

Details regarding the subject, particular cancer types and examples of cancer therapies are also discussed in detail above and the disclosure also applies here. The subject can be afflicted with breast cancer, in particular metastatic breast cancer.

Further Positive Response Markers

Also the expression of further biomarker RNA molecules, such as BRCA1 and PI3K, appeared to correlate with a positive response to therapy and therefore, could be useful either alone or in combination with other biomarker RNA molecules (see above) as positive response marker. Accordingly, in one embodiment, identifying in the combined analysis, preferably the combined expression profile, overexpression of BRCA1 as at least one biomarker RNA molecule in extracellular vesicles is indicative of progression-free survival. According to one embodiment, identifying in the combined analysis, preferably the combined expression profile, overexpression of BRCA1 as at least one biomarker RNA molecule in extracellular vesicles is indicative of therapy response.

According to one embodiment, identifying in the combined analysis, preferably the combined expression profile, overexpression of PI3K as at least one biomarker RNA molecule in circulating tumor cells and/or extracellular vesicles is indicative of progression-free survival. According to one embodiment, identifying in the combined analysis, preferably the combined expression profile, overexpression of PI3K as at least one biomarker RNA molecule in circulating tumor cells and/or extracellular vesicles is indicative of therapy response, respectively that the subject is benefitting from the therapy.

Details regarding the subject, particular cancer types and examples of cancer therapies are also discussed in detail above and the disclosure also applies here. The subject can be afflicted with breast cancer, in particular metastatic breast cancer.

Specific Correlation Pattern: No Overexpression of at Least One Biomarker RNA Molecule in CTCs and/or EVs is Related to a Positive Response to Therapy As has been discussed above, biomarker RNA molecules can also represent a positive response marker, if they are not overexpressed in CTCs and/or EVs, wherein no overexpression includes the absence of expression. E.g. if overexpression of such biomarker RNA molecule is not determined in CTCs and/or EVs, this can be indicative for a positive response to therapy. This e.g. applies to biomarkers that, if present respectively are overexpressed, are negative response markers (see above). Accordingly, absence of expression, respectively absence of overexpression of according biomarkers can be indicative for a positive response to therapy. Examples are provided in the following:

According to one embodiment, identifying in the combined analysis, preferably the combined expression profile, that AURKA as at least one biomarker RNA molecule is not overexpressed in extracellular vesicles and/or circulating tumor cells, preferably extracellular vesicles and optionally circulating tumor cells, is indicative of progression-free survival. According to one embodiment, identifying in the combined analysis, preferably the combined expression profile, that AURKA as at least one biomarker RNA molecule is not overexpressed in extracellular vesicles and/or circulating tumor cells, preferably extracellular vesicles and optionally circulating tumor cells, is indicative of therapy response, respectively that the subject is benefitting from the therapy. As has been discussed above, the therapy is in one embodiment a bone stabilization therapy, in particular involving the use of an anti-RANKL antibody such as denosumab. These findings are also relevant for and apply to the second aspect according to the present invention.

According to one embodiment, identifying in the combined analysis, preferably the combined expression profile, that at least the receptor tyrosine kinases HER2 and HER3 and preferably also cKIT and cMET as biomarker RNA molecules are not overexpressed in circulating tumor cells and/or extracellular vesicles, preferably circulating tumor cells and optionally extracellular vesicles, is indicative of progression-free survival. According to one embodiment, identifying in the combined analysis, preferably the combined expression profile, that at least the receptor tyrosine kinases HER2 and HER3, and preferably also cKIT and cMET as biomarker RNA molecules are not overexpressed in circulating tumor cells and/or extracellular vesicles, preferably circulating tumor cells and optionally extracellular vesicles, is indicative of therapy response, respectively that the subject is benefitting from the therapy. As has been discussed above, the therapy is in one embodiment chemotherapy.

According to one embodiment, identifying in the combined analysis, preferably the combined expression profile, that (i) at least the receptor tyrosine kinases HER2 and HER3 and preferably also cKIT and cMET as biomarker RNA molecules are not overexpressed in circulating tumor cells and/or extracellular vesicles and (ii) AURKA as at least one biomarker RNA molecule is not overexpressed in extracellular vesicles and/or circulating tumor cells is indicative of progression-free survival. According to one embodiment, identifying in the combined analysis, preferably the combined expression profile, that (i) at least the receptor tyrosine kinases HER2 and HER3 and preferably also cKIT and cMET as biomarker RNA molecules are not overexpressed in extracellular vesicles and/or circulating tumor cells and (ii) AURKA as at least one biomarker RNA molecule is not overexpressed in extracellular vesicles and/or circulating tumor cells is indicative of therapy response, respectively that the subject is benefitting from the therapy.

According to one embodiment, identifying in the combined analysis, preferably the combined expression profile, that (i) at least the receptor tyrosine kinases HER2 and HER3 and preferably also cKIT and cMET as biomarker RNA molecules are not overexpressed in circulating tumor cells and optionally extracellular vesicles and (ii) AURKA as at least one biomarker RNA molecule is not overexpressed in extracellular vesicles and optionally circulating tumor cells is indicative of progression-free survival and/or therapy response.

These biomarkers may also be combined with further positive response markers. Details are discussed elsewhere herein and it is referred to the according disclosure.

Details regarding the subject, particular cancer types and examples of cancer therapies are discussed in detail above, also in conjunction with the specific markers, and the disclosure also applies here. The subject can be afflicted with breast cancer, in particular metastatic breast cancer.

According to a second aspect a method for determining the effectiveness of a therapy in a subject or for predicting or monitoring therapy response in a patient is provided, comprising determining the expression level of AURKA in extracellular vesicles and optionally circulating tumor cells. As is demonstrated by the examples and explained above, detection of AURKA expression provides valuable information. It is referred to the above disclosure. These findings regarding the relevance of AURKA expression in extracellular vesicles as response marker were already explained and discussed in detail above and are also illustrated in the examples. It is referred to the above disclosure which also applies here. In brief, the examples demonstrate that if overexpression of AURKA is determined in extracellular vesicles, this was found to be indicative for a negative response to therapy, in particular to a bone stabilization therapy e.g. involving the use of an anti-RANKL antibody such as denosumab. As is demonstrated by the examples, the results obtained in EVs are significant by themselves. However, the results are improved, if the expression results of AURKA in CTCs are additionally taken into account. Moreover, the finding that AURKA as at least one biomarker RNA molecule is not overexpressed in extracellular vesicles, and optionally also not in circulating tumor cells, is indicative for a positive response to therapy and hence therapy response, respectively that the subject is benefitting from the therapy. As has been discussed above, the therapy is in one embodiment a bone stabilization therapy, in particular involving the use of an anti-RANKL antibody such as denosumab. Details regarding the subject, particular cancer types and examples of cancer therapies are discussed in detail above. The subject can be afflicted with breast cancer, in particular metastatic breast cancer.

Also disclosed are kits for use in the above described methods. Such kits may comprise e.g. one or more of the following:
One or more components for isolating circulating tumor cells;
One or more components for isolating extracellular vesicles;
One or more components for isolating RNA;
One or more reverse transcription polymerases;
One or more components for performing an amplification reaction, in particular for performing a quantitative PCR reaction, such as e.g. a DNA polymerase, primers or probes, e.g. one or more primer sets suitable for amplifying the biomarker RNA molecules described in detail above, respectively the corresponding cDNA.

Further Embodiments

Further embodiments of the present invention are described again in the following. The present invention in particular also provides for the following items:
1. A method for analysing the expression of one or more biomarker RNA molecules, comprising
  (A) isolating RNA from circulating tumor cells obtained from a subject, determining the expression of at least one biomarker RNA molecule in the isolated RNA and providing an expression profile based on the results;
  (B) isolating RNA from extracellular vesicles obtained from the subject, determining the expression of at least one biomarker RNA molecule in the isolated RNA and providing an expression profile based on the results; and
  (C) using the expression profiles determined in (A) and determined in (B) for a combined analysis of the results.
2. The method according to item 1, wherein the combined analysis comprises providing a combined expression profile using the expression profile determined in (A) and the expression profile determined in (B).
3. The method according to one or more of items 1 to 2, wherein the method comprises
  providing a liquid biological sample obtained from the subject;
  removing cells from the liquid biological sample, thereby providing a cell-depleted biological sample;
  isolating circulating tumor cells from the removed cells;
  wherein step (A) comprises isolating RNA from the isolated circulating tumor cells;
  wherein step (B) comprises isolating RNA from extracellular vesicles comprised in the cell-depleted biological sample.
4. The method according to one or more of items 1 to 2, wherein the method comprises
  providing a liquid biological sample obtained from the subject;
  isolating circulating tumor cells from the liquid biological sample;
  removing remaining cells from the liquid biological sample from which the circulating tumor cells were isolated thereby providing a cell-depleted biological sample;
  wherein step (A) comprises isolating RNA from the isolated circulating tumor cells;
  wherein step (B) comprises isolating RNA from extracellular vesicles comprised in the cell-depleted biological sample.
5. The method according to one or more of items 1 to 4, wherein the method comprises
  providing at least two liquid biological samples of the same kind obtained from the same subject;
  isolating circulating tumor cells from at least one of the liquid biological samples, wherein step (A) comprises isolating RNA from the isolated circulating tumor cells;
  obtaining a cell-depleted sample from at least one of the liquid biological samples, wherein step (B) comprises isolating RNA from extracellular vesicles comprised in the cell-depleted biological sample.
6. The method according to item 5, wherein the at least two biological samples of the same kind are obtained by aliquoting a biological sample obtained from the subject and/or wherein the at least two biological samples of the same kind were obtained from the same subject at the same time.
7. The method according to one or more of items 3 to 6, comprising isolating extracellular vesicles from the cell-depleted sample and wherein step (B) comprises isolating RNA from the extracellular vesicles.
8. The method according to one or more of items 1 to 7, wherein the method comprises isolating circulating tumor cells and/or extracellular vesicles by affinity capture.
9. The method according to one or more of items 1 to 8, wherein the extracellular vesicles comprise or predominantly consist of exosomes.
10. The method according to one or more of items 1 to 9, wherein RNA isolation in step (A) and/or step (B), preferably step (A) and (B), comprises binding RNA to a solid phase and eluting the RNA from the solid phase.
11. The method according to one or more of items 1 to 10, having one or more of the following characteristics:
  (i) wherein the RNA isolated in step (A) and/or step (B) comprises or consists of mRNA;
  (ii) wherein the RNA isolated in step (A) and/or step (B) comprises miRNA or essentially consists of small RNA up to 350 nt in length, up to 300 nt in length or up to 250 nt length, which includes miRNA.
12. The method according to one or more of items 1 to 11, wherein determining the expression of at least one biomarker RNA molecule in the isolated RNA in step (A) and/or step (B), preferably in step (A) and in step (B), comprises one or more of the following:
  (i) it comprises reverse transcription to obtain cDNA;
  (ii) it comprises at least one step of amplifying the cDNA; and/or
  (iii) it comprises performing a quantitative polymerase chain reaction.

13. The method according to one or more of items 1 to 12, in particular item 12, wherein determining the expression of at least one biomarker RNA molecule in the isolated RNA in step (A) and/or step (B), preferably step (A) and (B), comprises determining whether the at least one biomarker RNA molecule is overexpressed or not.

14. The method according to item 13, wherein a biomarker RNA molecule is determined to be overexpressed if its expression exceeds a defined threshold or cut-off.

15. The method according to one or more of items 1 to 14, wherein if the expression level of said biomarker RNA molecule is above a defined threshold or cut-off, the expression profile in (A) and/or (B) indicates that it is positive for said biomarker RNA molecule.

16. The method according to one or more of items 1 to 15, wherein determining the expression of at least one biomarker RNA molecule in the isolated RNA in step (A) and/or step (B), preferably step (A) and (B), comprises determining whether the expression level of the at least biomarker RNA molecule is higher than the expression level of that biomarker RNA molecule in a control or reference, e.g. determined in a healthy control or reference group if the subject is a cancer patient.

17. The method according to one or more of items 1 to 16, wherein the biological sample has one or more of the following characteristics:
    It is a liquid biopsy sample:
    It is a bodily fluid;
    It is selected from blood, urine, peritoneal effusions and pleural effusions, bone marrow aspirates and nipple aspirates;
    It is selected from blood and urine; and/or
    It is blood.

18. The method according to one or more of items 1 to 17, wherein the subject has one or more of the following characteristics:
    It is afflicted or suspected of being afflicted with a disease;
    It is afflicted or suspected of being afflicted with cancer, in particular solid cancer;
    It is afflicted or suspected of being afflicted with metastatic cancer;
    It is afflicted or suspected of being afflicted with breast cancer, prostate cancer, colon cancer, lung cancer, ovarian cancer, bladder cancer, pancreatic cancer, gastric cancer, liver cancer, sarcoma and melanoma;
    It is afflicted or suspected of being afflicted with breast cancer; and/or
    It is afflicted or suspected of being afflicted with metastatic breast cancer.

19. The method according to one or more of items 1 to 18, wherein the at least one biomarker RNA molecule has one or more of the following characteristics:
    It is selected from mRNA and miRNA
    It is mRNA.

20. The method according to one or more of items 1 to 19, wherein the at least one biomarker RNA molecule has one or more of the following characteristics:
    It is a cancer-associated tumor marker;
    It is a diagnostic, prognostic and/or predictive biomarker;
    It is a prognostic or predictive biomarker;
    It is associated with breast cancer, in particular metastatic breast cancer;
    It is a positive or negative response marker.

21. The method according to one or more of items 1 to 20, in particular items 13 to 20, wherein a biomarker panel is analysed in step (A) and/or step (B), preferably in step (A) and (B), wherein an according biomarker panel comprises 2 to 50, 5 to 100, 10 to 200, 20 to 250, 25 to 300 or 50 to 500 different biomarker RNA molecules.

22. The method according to item 21, wherein an according biomarker panel analyzed comprises biomarker RNA molecules selected from the biomarkers shown in Table I, wherein preferably an according biomarker panel comprises at least 2, at least 3, at least 5, at least 7, at least 10 or at least 15 biomarker RNA molecules corresponding to the biomarkers shown in Table I, and wherein more preferably an according biomarker RNA molecule panel is analyzed in step (A) and step (B) using appropriate primers in an amplification reaction.

23. The method according to one or more of items 1 to 22, in particular 21 or 22, wherein the at least one RNA biomarker molecule is selected from
    (i) the group consisting of transcripts of genes for an epithelial like phenotype, transcripts of genes for a basal-like phenotype, transcripts of genes for tyrosine kinase receptors, transcripts of genes for factors related to therapy resistance, transcripts of genes for factors related to epithelial to mesenchymal transition or tumor stem cells, transcripts of genes for factors involved in the steroid receptor pathway and transcripts of genes for factors involved in immune modulation; preferably transcripts of according genes as shown in Table I;
    (ii) the group consisting of transcripts of genes for a basal-like phenotype, transcripts of genes for tyrosine kinase receptors, transcripts of genes for factors related to therapy resistance, transcripts of genes for factors related to epithelial to mesenchymal transition or tumor stem cells; preferably transcripts of according genes as shown in Table I;
    (iii) the group consisting of AKT2, ALK, AR, AURKA, BRCA1, cKIT, cMET, EGFR, ERCC1, HER2, HER3, KRT5, mTOR, NOTCH1, PARP1, P13K and SRC1;
    (iv) the group consisting of HER2, HER3, cKIT, cMET, AURKA, mTOR and ERCC1; and/or
    (v) the group consisting of HER2, HER3, cKIT, cMET, AURKA and mTOR.

24. The method according to item 23, for analyzing the expression of at least two, at least three, at least four, at least five, at least seven, at least ten or at least fifteen biomarker RNA molecules.

25. The method according to one or more of items 1 to 24, in particular items 13 to 24, wherein at least the expression of the following one or more RNA biomarker molecules is determined in step (A) and step (B) that are selected from:
    (i) HER2;
    (ii) HER3;
    (iii) HER2 and HER3;
    (iv) AURKA;
    (v) mTOR;
    (vi) HER2, HER3, cMET and cKIT;
    (vii) HER2, HER3, cMET, cKIT and AURKA;
    (viii) HER2, HER3, cMET, cKIT, AURKA and mTOR; and/or
    (ix) HER2, HER3, cKIT, cMET, AURKA, mTOR and ERCC1.

26. The method according to one or more of items 1 to 25, in particular items 13 to 25, wherein the expression of at least one identical biomarker RNA molecule is determined in step (A) and step (B).

27. The method according to one or more of items 1 to 26, in particular items 13 to 26 or items 21 to 26, wherein the expression of the same biomarker RNA molecules is determined in step (A) and step (B).

28. The method according to one or more of items 1 to 27, wherein the method encompasses determining the expression of at least one diverging biomarker RNA molecule in step (A) and step (B).

29. The method according to one or more of items 1 to 28, in particular items 21 to 28, wherein the expression profile provided in step (A) and/or step (B), preferably step (A) and step (B), comprises the results of analysed RNA biomarkers that are determined to be overexpressed, and optionally additionally comprises results of analysed RNA biomarkers that are not determined to be overexpressed.

30. The method according to one or more of items 1 to 29, in particular items 21 to 29, wherein step (C) comprises using from the expression profile determined in step (A) and/or determined in step (B), preferably step (A) and step (B), results of analysed RNA biomarkers determined to be overexpressed for the combined analysis of the results.

31. The method according to one or more of items 1 to 30, in particular items 21 to 30, wherein step (C) comprises using from the expression profile determined in step (A) and/or determined in step (B), preferably step (A) and step (B), results of analysed RNA biomarkers determined to be overexpressed and additionally results of analysed RNA biomarkers that are not determined to be overexpressed in step (A) and/or step (B) for the combined analysis of the results.

32. The method according to one or more of items 2 to 31, in particular items 21 to 31, wherein step (C) comprises using from the expression profile determined in step (A) and/or determined in step (B) results of RNA biomarkers determined to be overexpressed for providing the combined expression profile.

33. The method according to one or more of items 2 to 32, in particular items 21 to 32, wherein the combined expression profile provided in step (C) comprises results of analysed RNA biomarkers that are determined to be overexpressed in step (A) and/or step (B) and additionally comprises results of analysed RNA biomarkers that are not determined to be overexpressed in step (A) and/or step (B), wherein preferably the according results from (A) and (B) are comprised.

34. The method according to one or more of items 1 to 33, in particular items 20 to 33, wherein the method further comprises using the results of the combined analysis, preferably the combined expression profile, for medical prognosis, diagnosis and/or treatment choice, or for predicting or monitoring response to therapy.

35. The method according to item 34, wherein the subject is predicted to respond, or not respond to therapy based on the results of the combined analysis or preferably, the combined expression profile.

36. The method according to one or more of items 1 to 35, in particular items 20 to 35, wherein the method is a method of determining the effectiveness of a therapy administered to a human subject afflicted with cancer.

37. The method according to one or more of items 34 to 36, wherein the therapy has one or more of the following characteristics:
   It is a cancer therapy;
   It is a cancer therapy selected from chemotherapy, hormone therapy, targeted therapy, immunotherapy, therapy with angiogenesis inhibitors and radiotherapy;
   It is a cancer therapy comprising treatment with a therapeutic antibody;
   It is a cancer therapy comprising bone stabilization therapy;
   It is a cancer therapy comprising bone stabilization therapy, wherein the bone stabilization therapy comprises treatment with an anti-RANKL-antibody and/or bisphosphonates; and/or
   It is a cancer therapy comprising bone stabilization therapy, wherein the bone stabilization therapy comprises treatment with the anti-RANKL-antibody denosumab and/or bisphosphonates.

38. The method according to one or more of items 1 to 37, in particular items 20 to 37, wherein the method further comprises using the results of the combined analysis, preferably the combined expression profile, for classifying the subject based on the expression profiles determined in (A) and (B) and analysed in (C).

39. The method according to one or more of items 1 to 38, in particular items 20 to 38, wherein the method further comprises using the results of the combined analysis, preferably the combined expression profile, for predicting or detecting cancer progression.

40. The method according to one or more of items 1 to 39, in particular items 20 to 39, wherein the method further comprises using the results of the combined analysis, preferably the combined expression profile, for therapy stratification.

41. The method according to one or more of items 1 to 40, in particular items 20 to 40, preferably 21 to 40, more preferably items 23 to 40, wherein the method comprises performing steps (A) to (C) at different time points and comparing the results.

42. The method according to one or more of items 1 to 41, in particular items 20 to 41, wherein identifying in the combined analysis, preferably the combined expression profile, overexpression of at least one biomarker RNA molecule in circulating tumor cells and/or extracellular vesicles is indicative of disease progression, therapy failure or resistance to therapy.

43. The method according to one or more of items 1 to 42, in particular items 20 to 42, wherein identifying in the combined analysis, preferably the combined expression profile, overexpression of at least one biomarker RNA molecule in circulating tumor cells and/or extracellular vesicles is indicative that the therapeutic agent is ineffective.

44. The method according to item 42 or 43, wherein identifying in the combined analysis, preferably the combined expression profile, overexpression of at least one biomarker RNA molecule in circulating tumor cells and optionally extracellular vesicles is indicative of disease progression, therapy failure or resistance to therapy.

45. The method according to item 42 or 43, wherein identifying in the combined analysis, preferably the combined expression profile, overexpression of at least one biomarker RNA molecule in circulating tumor cells and optionally extracellular vesicles is indicative that the therapeutic agent is ineffective.

46. The method according to item 42 or 43, wherein identifying in the combined analysis, preferably the combined expression profile, overexpression of the at least one biomarker RNA molecule in extracellular vesicles and optionally circulating tumor cells is indicative of disease progression, therapy failure or resistance to therapy.

47. The method according to item 42 or 43, wherein identifying in the combined analysis, preferably the combined expression profile, overexpression of the at least one biomarker RNA molecule in extracellular vesicles and optionally circulating tumor cells is indicative that the therapeutic agent is ineffective.

48. The method according to one or more of items 1 to 41, in particular items 20 to 41, wherein identifying in the combined analysis, preferably the combined expression profile, overexpression of at least one biomarker RNA molecule in extracellular vesicles but not in circulating tumor cells is indicative of disease progression.

49. The method according to one or more of items 1 to 41, in particular items 20 to 41, wherein identifying in the combined analysis, preferably the combined expression profile, overexpression of at least one biomarker RNA molecule in extracellular vesicles but not in circulating tumor cells is indicative of therapy failure or resistance to therapy.

50. The method according to one or more of items 1 to 41, in particular items 20 to 41, wherein identifying in the combined analysis, preferably the combined expression profile, overexpression of at least one biomarker RNA molecule in extracellular vesicles but not in circulating tumor cells is indicative that the therapeutic agent is ineffective.

51. The method according to one or more of items 1 to 41, in particular items 20 to 41, wherein identifying in the combined analysis, preferably the combined expression profile, overexpression of at least one biomarker RNA molecule in circulating tumor cells but not in extracellular vesicles is indicative of disease progression.

52. The method according to one or more of items 1 to 41, in particular items 20 to 41, wherein identifying in the combined analysis, preferably the combined expression profile, overexpression of at least one biomarker RNA molecule in circulating tumor cells but not in extracellular vesicles is indicative of therapy failure or resistance to therapy.

53. The method according to one or more of items 1 to 41, in particular items 20 to 41, wherein identifying in the combined analysis, preferably the combined expression profile, overexpression of at least one biomarker RNA molecule in circulating tumor cells but not in extracellular vesicles is indicative that the therapeutic agent is ineffective.

54. The method according to one or more of items 1 to 41, in particular items 20 to 41, wherein identifying in the combined analysis, preferably the combined expression profile, overexpression of at least one biomarker RNA molecule in circulating tumor cells and/or extracellular vesicles is indicative of progression-free survival.

55. The method according to one or more of items 1 to 41, in particular items 20 to 41, wherein identifying in the combined analysis, preferably the combined expression profile, overexpression of at least one biomarker RNA molecule in circulating tumor cells and/or extracellular vesicles is indicative of therapy response.

56. The method according to item 54 or 55, wherein identifying in the combined analysis, preferably the combined expression profile, overexpression of at least one biomarker RNA molecule in circulating tumor cells and optionally extracellular vesicles is indicative of progression-free survival.

57. The method according to item 54 or 55, wherein identifying in the combined analysis, preferably the combined expression profile, overexpression of at least one biomarker RNA molecule in circulating tumor cells and optionally extracellular vesicles is indicative of therapy response.

58. The method according to item 54 or 55, wherein identifying in the combined analysis, preferably the combined expression profile, overexpression of at least one biomarker RNA molecule in extracellular vesicles and optionally circulating tumor cells is indicative of progression-free survival.

59. The method according to item 54 or 55, wherein identifying in the combined analysis, preferably the combined expression profile, overexpression of at least one biomarker RNA molecule in extracellular vesicles and optionally circulating tumor cells is indicative of therapy response.

60. The method according to item 54 or 55, wherein identifying in the combined analysis, preferably the combined expression profile, overexpression of at least one biomarker RNA molecule in circulating tumor cells but not in extracellular vesicles is indicative of progression-free survival and/or therapy response.

61. The method according to item 54 or 55, wherein identifying in the combined analysis, preferably the combined expression profile, overexpression of at least one biomarker RNA molecule in extracellular vesicles but not circulating tumor cells is indicative of progression-free survival and/or therapy response.

62. The method according to one or more of items 1 to 41, in particular to items 20 to 41, wherein identifying in the combined analysis, preferably the combined expression profile, that at least one biomarker RNA molecule is not overexpressed in circulating tumor cells and/or extracellular vesicles is indicative of progression-free survival.

63. The method according to one or more of items 1 to 41, in particular to items 20 to 41, wherein identifying in the combined analysis, preferably the combined expression profile, that at least one biomarker RNA molecule is not overexpressed in circulating tumor cells and/or extracellular vesicles is indicative of therapy response.

64. The method according to item 62 or 63, wherein identifying in the combined analysis, preferably the combined expression profile, that at least one biomarker RNA molecule is not overexpressed in circulating tumor cells and optionally extracellular vesicles is indicative of progression-free survival.

65. The method according to item 62 or 63, wherein identifying in the combined analysis, preferably the combined expression profile, that at least one biomarker RNA molecule is not overexpressed in circulating tumor cells and optionally extracellular vesicles is indicative of therapy response.

66. The method according to item 62 or 63, wherein identifying in the combined analysis, preferably the combined expression profile, that at least one biomarker RNA molecule is not overexpressed in extracellular vesicles and optionally circulating tumor cells is indicative of progression-free survival.

67. The method according to item 62 or 63, wherein identifying in the combined analysis, preferably the combined expression profile, that at least one biomarker RNA molecule is not overexpressed in extracellular vesicles and optionally circulating tumor cells is indicative of therapy response.

68. The method according to one or more of items 1 to 41, in particular items 23 to 41, wherein identifying in the combined analysis, preferably the combined expression profile, overexpression of at least one receptor tyrosine kinase as biomarker RNA molecule in circulating tumor cells and/or extracellular vesicles is indicative of disease progression.

69. The method according to one or more of items 1 to 41, in particular to items 23 to 41, wherein identifying in the combined analysis, preferably the combined expression profile, overexpression of at least one receptor tyrosine kinase as biomarker RNA molecule in circulating tumor cells and/or extracellular vesicles is indicative of therapy failure or resistance to therapy.

70. The method according to one or more of items 1 to 41, in particular 23 to 41, wherein identifying in the combined analysis, preferably the combined expression profile, overexpression of at least one receptor tyrosine kinase as biomarker RNA molecule in circulating tumor cells and/or extracellular vesicles is indicative that the therapeutic agent is ineffective.

71. The method according to item 68, wherein identifying in the combined analysis, preferably the combined expression profile, overexpression of at least one receptor tyrosine kinase as biomarker RNA molecule in circulating tumor cells and optionally extracellular vesicles is indicative of disease progression.

72. The method according to item 69, wherein identifying in the combined analysis, preferably the combined expression profile, overexpression of at least one receptor tyrosine kinase as biomarker RNA molecule in circulating tumor cells and optionally extracellular vesicles is indicative of therapy failure or resistance to therapy.

73. The method according to item 70, wherein identifying in the combined analysis, preferably the combined expression profile, overexpression of at least one receptor tyrosine kinase as biomarker RNA molecule in circulating tumor cells and optionally extracellular vesicles is indicative that the therapeutic agent is ineffective.

74. The method according to one or more of items 68 to 73, having one or more of the following characteristics:
    The expression of at least two, at least three or at least four receptor tyrosine kinases is determined in step (A) and/or step (B), preferably step (A) and step (B);
    The receptor tyrosine kinase is selected from HER2, HER3, cKIT and cMET;
    The receptor tyrosine kinase is selected from HER2, HER3, cKIT and cMET and the expression of at least two, at least three or all four of these receptor tyrosine kinases is determined in step (A) and/or step (B), preferably step (A) and step (B).

75. The method according to one or more of items 68 to 74, wherein the therapy is or comprises chemotherapy.

76. The method according to one or more of items 68 to 75, wherein the subject is a patient afflicted with breast cancer, in particular metastatic breast cancer.

77. The method according to one or more of items 68 to 76, further comprising treating the subject with a different therapeutic agent, e.g. targeted cancer therapy.

78. The method according to one or more of items 1 to 41, in particular to items 21 to 41, wherein identifying in the combined analysis, preferably the combined expression profile, overexpression of AURKA as at least one biomarker RNA molecule in extracellular vesicles and/or circulating tumor cells is indicative of disease progression.

79. The method according to one or more of items 1 to 41, in particular to items 21 to 41, wherein identifying in the combined analysis, preferably the combined expression profile, overexpression of AURKA as at least one biomarker RNA molecule in extracellular vesicles and/or circulating tumor cells is indicative of therapy failure or resistance to therapy.

80. The method according to one or more of items 1 to 41, in particular to items 21 to 41, wherein identifying in the combined analysis, preferably the combined expression profile, overexpression of AURKA as at least one biomarker RNA molecule in extracellular vesicles and/or circulating tumor cells is indicative that the therapeutic agent is ineffective.

81. The method according to item 78, wherein identifying in the combined analysis, preferably the combined expression profile, overexpression of AURKA as at least one biomarker RNA molecule in extracellular vesicles and optionally circulating tumor cells is indicative of disease progression.

82. The method according to item 79, wherein identifying in the combined analysis, preferably the combined expression profile, overexpression of AURKA as at least one biomarker RNA molecule in extracellular vesicles and optionally circulating tumor cells is indicative of therapy failure or resistance to therapy.

83. The method according to item 80, wherein identifying in the combined analysis, preferably the combined expression profile, overexpression of AURKA as at least one biomarker RNA molecule in extracellular vesicles and optionally circulating tumor cells is indicative that the therapeutic agent is ineffective.

84. The method according to one or more of items 78 to 83, wherein the therapy is or comprises a bone stabilization therapy, in particular involving the use of an anti-RANKL antibody, more preferably denosumab.

85. The method according to one or more of items 78 to 84, wherein the subject is a patient afflicted with breast cancer, in particular metastatic breast cancer.

86. The method according to one or more of items 78 to 85, further comprising treating the subject with a different therapeutic agent.

87. The method according to one or more of items 1 to 41, in particular to items 21 to 41, wherein identifying in the combined analysis, preferably the combined expression profile, overexpression of mTOR as at least one biomarker RNA molecule in extracellular vesicles is indicative of disease progression.

88. The method according to one or more of items 1 to 41, in particular to items 21 to 41, wherein identifying in the combined analysis, preferably the combined expression profile, overexpression of mTOR as at least one biomarker RNA molecule in extracellular vesicles is indicative of therapy failure or resistance to therapy.

89. The method according to one or more of items 1 to 41, in particular to items 21 to 41, wherein identifying in the combined analysis, preferably the combined expression profile, overexpression of mTOR as at least one biomarker RNA molecule in extracellular vesicles is indicative that the therapeutic agent is ineffective.

90. The method according to one or more of items 1 to 41, in particular to items 21 to 41, wherein identifying in the combined analysis, preferably the combined expression profile, (i) overexpression of at least one receptor tyrosine kinase as biomarker RNA molecule in circulating tumor cells and (ii) overexpression of AURKA as at least one biomarker RNA molecule in extracellular vesicles is indicative of disease progression.

91. The method according to one or more of items 1 to 41, in particular to items 21 to 41, wherein identifying in the combined analysis, preferably the combined expression profile, (i) overexpression of at least one receptor tyrosine kinase as biomarker RNA molecule in circulating tumor cells and (ii) overexpression of AURKA as at least one biomarker RNA molecule in extracellular vesicles is indicative of therapy failure or resistance to therapy.

92. The method according to one or more of items 1 to 41, in particular to items 21 to 41, wherein identifying in the combined analysis, preferably the combined expression profile, (i) overexpression of at least one receptor tyrosine kinase as biomarker RNA molecule in circulating tumor cells and (ii) overexpression of AURKA as at least one biomarker RNA molecule in extracellular vesicles is indicative that the therapeutic agent is ineffective.

93. The method according to one or more of items 90 to 92, having one or more of the following characteristics:
    The expression of at least two, at least three or at least four receptor tyrosine kinases is determined;
    The receptor tyrosine kinase is selected from HER2, HER3, cKIT and cMET; and/or
    The receptor tyrosine kinase is selected from HER2, HER3, cKIT and cMET and the expression of at least two, at least three or all four of these receptor tyrosine kinases is determined.

94. The method according to one or more of items 90 to 93, wherein the subject is a patient afflicted with breast cancer, in particular metastatic breast cancer.

95. The method according to one or more of items 90 to 94, wherein the therapy is or comprises chemotherapy and/or bone stabilization therapy, in particular a bone stabilization therapy involving the use of an anti-RANKL antibody, more preferably denosumab.

96. The method according to one or more of items 90 to 95, wherein the finding is indicative of chemotherapy and denosumab failure.

97. The method according to one or more of items 90 to 96, further comprising treating the subject with a different therapeutic agent, e.g. targeted cancer therapy.

98. The method according to one or more of items 1 to 41, in particular to items 21 to 41, wherein identifying in the combined analysis, preferably the combined expression profile, overexpression of ERCC1 as at least one biomarker RNA molecule in extracellular vesicles is indicative of disease progression, is indicative of therapy failure or resistance to therapy and/or is indicative that the therapeutic agent is ineffective.

99. The method according to one or more of items 1 to 41, in particular to items 21 to 41, wherein identifying in the combined analysis, preferably the combined expression profile, overexpression of AR as at least one biomarker RNA molecule in extracellular vesicles is indicative of disease progression, is indicative of therapy failure or resistance to therapy and/or is indicative that the therapeutic agent is ineffective.

100. The method according to one or more of items 1 to 41, in particular to items 21 to 41, wherein identifying in the combined analysis, preferably the combined expression profile, overexpression of KRT5 as at least one biomarker RNA molecule in extracellular vesicles is indicative of disease progression, is indicative of therapy failure or resistance to therapy and/or is indicative that the therapeutic agent is ineffective.

101. The method according to one or more of items 1 to 41, in particular to items 21 to 41, wherein identifying in the combined analysis, preferably the combined expression profile, overexpression of mTOR as at least one biomarker RNA molecule in circulating tumor cells is indicative of progression-free survival.

102. The method according to one or more of items 1 to 41, in particular to items 21 to 41, wherein identifying in the combined analysis, preferably the combined expression profile, overexpression of mTOR as at least one biomarker RNA molecule in circulating tumor cells is indicative of therapy response.

103. The method according to one or more of items 1 to 41, in particular to items 21 to 41, wherein identifying in the combined analysis, preferably the combined expression profile, overexpression of BRCA1 as at least one biomarker RNA molecule in extracellular vesicles is indicative of progression-free survival and/or therapy response.

104. The method according to one or more of items 1 to 41, in particular to items 21 to 41, wherein identifying in the combined analysis, preferably the combined expression profile, overexpression of P13K as at least one biomarker RNA molecule in circulating tumor cells and/or extracellular vesicles is indicative of progression-free survival and/or therapy response.

105. The method according to one or more of items 1 to 41, in particular to items 21 to 41, wherein identifying in the combined analysis, preferably the combined expression profile, that AURKA as at least one biomarker RNA molecule is not overexpressed in extracellular vesicles and/or circulating tumor cells is indicative of progression-free survival.

106. The method according to one or more of items 1 to 41, in particular to items 21 to 41, wherein identifying in the combined analysis, preferably the combined expression profile, that AURKA as at least one biomarker RNA molecule is not overexpressed in extracellular vesicles and/or circulating tumor cells is indicative of therapy response.

107. The method according to item 105 or 106, wherein the therapy is or comprises a bone stabilization therapy, in particular involving denosumab.

108. The method according to one or more of items 1 to 41, in particular to items 21 to 41, wherein identifying in the combined analysis, preferably the combined expression profile, that at least the receptor tyrosine kinases HER2 and HER3 and preferably also cKIT and cMET as biomarker RNA molecules are not overexpressed in circulating tumor cells and/or extracellular vesicles is indicative of progression-free survival.

109. The method according to one or more of items 1 to 41, in particular to items 21 to 41, wherein identifying in the combined analysis, preferably the combined expression profile, that at least the receptor tyrosine kinases HER2 and HER3, and preferably also cKIT and cMET as biomarker RNA molecules are not overexpressed in circulating tumor cells and/or extracellular vesicles is indicative of therapy response.

110. The method according to items 108 or 109, wherein the therapy is or involves chemotherapy, and wherein optionally the subject is afflicted with cancer, preferably selected from solid cancer, metastatic cancer, breast cancer and metastatic breast cancer.

111. The method according to one or more of items 1 to 41, in particular to items 21 to 41. wherein identifying in the combined analysis, preferably the combined expression profile, that (i) at least the receptor tyrosine kinases HER2 and HER3 and preferably also cKIT and cMET as biomarker RNA molecules are not overexpressed in circulating tumor cells and/or extracellular vesicles and (ii) AURKA as at least one biomarker RNA molecule is not overexpressed in extracellular vesicles and/or circulating tumor cells is indicative of progression-free survival.

112. The method according to one or more of items 1 to 41, in particular to items 21 to 41, wherein identifying in the combined analysis, preferably the combined expression profile, that (i) at least the receptor tyrosine kinases HER2 and HER3 and preferably also cKIT and cMET as biomarker RNA molecules are not overexpressed in circulating tumor cells and/or extracellular vesicles and (ii) AURKA as at least one biomarker RNA molecule is not overexpressed in in extracellular vesicles and/or circulating tumor cells is indicative of therapy response.

113. The method according to one or more of items 1 to 41, in particular to items 21 to 41, wherein identifying in the combined analysis, preferably the combined expression profile, that (i) at least the receptor tyrosine kinases HER2 and HER3 and preferably also cKIT and cMET as biomarker RNA molecules are not overexpressed in circulating tumor cells and optionally extracellular vesicles and (ii) AURKA as at least one biomarker RNA molecule is not overexpressed in extracellular vesicles and optionally circulating tumor cells is indicative of progression-free survival.

114. The method according to one or more of items 1 to 41, in particular to items 21 to 41, wherein identifying in the combined analysis, preferably the combined expression profile, that (i) at least the receptor tyrosine kinases HER2 and HER3 and preferably also cKIT and cMET as biomarker RNA molecules are not overexpressed in circulating tumor cells and optionally extracellular vesicles and (ii) AURKA as at least one biomarker RNA molecule is not overexpressed in extracellular vesicles and optionally circulating tumor cells is indicative of therapy response.

115. The method according to item 108, wherein identifying in the combined analysis, preferably the combined expression profile, that at least the receptor tyrosine kinases HER2 and HER3, and preferably also cKIT and cMET as biomarker RNA molecules are not overexpressed in circulating tumor cells and optionally extracellular vesicles is indicative of progression-free survival.

116. The method according to item 109, wherein identifying in the combined analysis, preferably the combined expression profile, that that at least the receptor tyrosine kinases HER2, HER3, and preferably also cKIT and cMET as biomarker RNA molecules are not overexpressed in circulating tumor cells and optionally extracellular vesicles is indicative of therapy response.

117. The method according to one or more of items 111 to 116, in particular to items 114 to 116, wherein the therapy is or involves chemotherapy, and wherein optionally the subject is afflicted with cancer, preferably selected from solid cancer, metastatic cancer, breast cancer and metastatic breast cancer 118. The method according to item 105, wherein identifying in the combined analysis, preferably the combined expression profile, that AURKA as at least one biomarker RNA molecule is not overexpressed in extracellular vesicles and optionally circulating tumor cells is indicative of progression-free survival.

119. The method according to item 106, wherein identifying in the combined analysis, preferably the combined expression profile, that AURKA as at least one biomarker RNA molecule is not overexpressed in extracellular vesicles and optionally circulating tumor cells is indicative of therapy response.

120. The method according to one or more of items 118 or 119, wherein the therapy is or comprises a bone stabilization therapy, in particular with denosumab.

121. A method for determining the effectiveness of a therapy in a subject or predicting or monitoring therapy response, comprising determining the expression level of AURKA in extracellular vesicles and optionally circulating tumor cells.

As is demonstrated by the examples and explained above, detection of AURKA expression provides valuable information as negative or positive response marker. It is referred to the above disclosure.

122. The method according to item 121, wherein overexpression of AURKA in extracellular vesicles and optionally in circulating tumor cells is a negative response marker.

123. The method according to item 121, wherein overexpression of AURKA in extracellular vesicles and optionally in circulating tumor cells is indicative of disease progression.

124. The method according to item 121, wherein overexpression of AURKA in extracellular vesicles and optionally in circulating tumor cells is indicative of therapy failure or resistance to therapy.

125. The method according to item 121, wherein overexpression of AURKA in extracellular vesicles and optionally in circulating tumor cells indicates that the therapeutic agent is ineffective.

126. The method according to item 121, wherein identifying that AURKA is not overexpressed in extracellular vesicles and optionally circulating tumor cells is indicative of progression-free survival.

127. The method according to item 121, wherein identifying that AURKA is not overexpressed in extracellular vesicles and optionally circulating tumor cells is indicative of therapy response.

128. The method according to one or more of items 121 to 127, wherein the therapy is or comprises a bone stabilization therapy, in particular involving the use of an anti-RANKL antibody, more preferably denosumab.

129. The method according to one or more of items 121 to 128, wherein the subject is a patient afflicted with breast cancer, in particular metastatic breast cancer.

130. The method according to one or more of items 121 to 129, further comprising treating the subject with a different therapeutic agent.

These findings regarding the relevance of AURKA expression as response marker were already explained and discussed in detail above and are also illustrated in the examples. The details have been discussed in detail above and it is referred to the according disclosure. It is also referred to the above disclosure and the examples regarding the further details for example for determining expression and/or overexpression of AURKA. It is also referred to the above disclosure for the methods for isolating RNA from extracellular vesicles and/or circulating tumor cells. It is also referred to the above disclosure regarding the details for isolating extracellular and/or circulating tumor cells from biological samples. It is also referred to the above disclosure with respect to the patient characteristics and therapies.

This invention is not limited by the exemplary methods and materials disclosed herein, and any methods and materials similar or equivalent to those described herein can be used in the practice or testing of embodiments of this invention. Numeric ranges are inclusive of the numbers defining the range. The headings provided herein are not limitations of the various aspects or embodiments of this invention which can be read by reference to the specification as a whole.

As used in the subject specification and claims, the singular forms "a", "an" and "the" include plural aspects unless the context clearly dictates otherwise. Reference to "the disclosure" and "the invention" and the like includes single or multiple aspects taught herein; and so forth. Aspects taught herein are encompassed by the term "invention".

According to one embodiment, subject matter described herein as comprising certain steps in the case of methods or as comprising certain features or components refers to subject matter consisting of the respective steps or features or components.

It is preferred to select and combine preferred embodiments described herein and the specific subject-matter arising from a respective combination of preferred embodiments also belongs to the present disclosure.

EXAMPLES

The invention is illustrated by the following non-limiting examples.

Example 1

Patients and Sample Collection Blood was collected from 30 metastatic breast cancer (MBC) patients at the time of disease progression (T0) and at two consecutive clinical staging time points (T1 and T2) during therapy resulting in a total of 90 blood samples (3 samples of each MBC patient).

In the course of the therapy, these 30 MBC patients which were non-responders at T0 were again assigned to responders or non-responders at the two consecutive clinical staging time points (T1 and T2). Therapy responders and therapy non-responders were identified according to RECIST criteria.

The collected blood samples were processed as follows:
a) Isolation of Circulating Tumor Cells (CTCs)

CTCs were isolated from 5 ml blood by positive immunomagnetic selection targeting EpCAM, EGFR and HER2 (AdnaTest EMT2/StemCell Select™, QIAGEN; according to the manufacturers instructions). In short, circulating tumor cells were labeled with immunomagnetic beads targeting epithelial- and tumor-associated antigens (EpCAM, EGFR and HER2) and separated by a magnetic particle concentrator. The separated cells were lysed (Adnalysis buffer) and mRNA was then purified from these lysates via Oligo (dT)25-coated magnetic beads as described in further detail below.

b) Isolation of Extracellular Vesicles (EV) and Isolation of Vesicular Total RNA Isolation of total RNA from extracellular vesicles was done according to the manufacturer's protocol from 4 ml pre-filtered plasma by using a two-step (extracellular vesicle purification and total RNA isolation) affinity-based binding to a spin column (exoRNeasy, QIAGEN). In short, for the extracellular vesicle purification step, prefiltered plasma (with particles larger than 0.8 μM excluded) was mixed with Buffer XBP and bound to an exoEasy membrane affinity spin column. The bound extracellular vesicles were washed with Buffer XWP, and then lysed with QIAzol.

In the RNA extraction step, chloroform was added to the QIAzol lysate and the aqueous phase was recovered and mixed with ethanol. Total RNA was bound to a spin column, where it was washed three times and eluted.

c) Isolation of mRNA from (i) the CTC Lysate and (ii) the Vesicular Total RNA and Reverse Transcription mRNA was then purified from (i) the CTC lysate and (ii) the total vesicular RNA via Oligo (dT)25-coated magnetic beads according to the manufacturer's instructions (AdnaTest EMT2/StemCell Detect™, QIAGEN). Thereby, two separate mRNA fractions were obtained, namely (i) CTC derived mRNA and (ii) EV derived mRNA.

The isolated mRNA was then reverse transcribed into cDNA according to the manufacturer's protocol (AdnaTest EMT2/StemCell Detect™, QIAGEN), thereby generating two separate cDNA fractions, namely (i) CTC derived cDNA and (ii) EV derived cDNA.

d) Generation of CTC and EV Expression Profiles

The CTC derived cDNA and the EV derived cDNA was subsequently pre-amplified and analysed by a multimarker qPCR (AdnaPanel TNBC, QIAGEN). RNA profiles of 17 biomarker genes (including AKT2, ALK, AR, AURKA, BRCA1, cKIT, cMET, EGFR, ERCC1, HER2, HER3, KRT5, mTOR, NOTCH1, PARP1, P13K and SRC1) and GAPDH were obtained; CD45 served as leukocyte control.

For each gene, the obtained expression data was normalized by expression data of healthy donors (n=20) for the according gene. For each gene, a mean expression was determined based on the data of the healthy donors (blood for CTCs and plasma for EVs). The cut-off/threshold (mean value plus required standard deviation) for overexpression was set to achieve a specificity of at least 90% for each gene in CTCs and EVs. Therefore, different thresholds/cut-offs were determined for each gene in CTCs and EVs. The according sample Ct was then subtracted from the cut-off. It can be assumed that several of the genes of interest are e.g. not exclusively expressed in CTCs but also, to a certain amount, in contaminating leukocytes (approx. 1000 leukocytes per sample). Therefore, a CD45 normalizer was included to calculate a leukocyte contribution to each gene (building a ΔΔCt value). Leukocyte titration experiments showed that two correlations should be considered:

1. Some genes of interest might not be expressed in leukocytes. Therefore, for such genes no leukocyte correction is necessary. Here, the calculation can be performed as follows: $\Delta Ct=(CutOff_{(gene)}-SampleCt_{(gene)})$
2. Expression of both the gene of interest and of CD45 increases with increasing numbers of leukocytes contaminating the CTC preparation. When displayed in a graph with logarithmic scale, the two curves run parallel to each other. This means that the gene of interest leads to a background signal dependent on the leukocyte count in the CTC fraction. To eliminate the contribution of leukocytes to the expression level of the gene of interest and thus to avoid false positive results, the specific expression level of the gene of interest was calculated based on the ΔΔCt. $\Delta\Delta Ct=(CutOff_{(gene)}-SampleCt_{gene})-(CutOff_{(CD45)}-SampleCt_{(CD45)})$. This leukocyte leukocyte correction based on CD45 was also integrated for genes that were found to be expressed at a lower level in leukocytes. E.g. the results discussed below for receptor tyrosine kinases, mTor and AURKA were calculated based on the ΔΔCt.

CutOff(gene)=threshold/cut-off of the biomarker in healthy donors (mean value+required standard deviation to achieve 90% specificity)

SampleCt(gene)=expression of gene in patient sample (EV or CTC)

CutOff(CD45)=threshold/cut-off of CD45 in healthy donors

SampleCt(CD45)=expression of CD45 in patient sample (CTC or EV)

For the EV and CTC expression profile, a sample was determined to be positive for the individual RNA biomarker if the result was above 0. A sample (CTC or EV) was determined to be negative if the result was 0 or lower.

Results

In general, data analysis showed great differences in the RNA expression profiles in EVs and CTCs. Of all 17 biomarker genes analyzed the overall positive signal observation was 223 of 1530 (15%) for CTCs and 108/1462

(7.4%) for EVs and the overlapping signals in CTCs and EVs was 18/1530 (1%) only. Accordingly, the frequencies of signals differed in EVs and CTCs and only a small number of matched overexpression signals in CTCs and EVs was found for the analyzed biomarker RNA molecules.

It was found that the information obtained from analysis of the CTC expression profile and the EV expression profile was highly complementary and additive in improving e.g. prognostic and predictive results regarding therapy responsiveness. Therefore, using the determined CTC expression profile and the determined EV expression profile for a combined analysis of the results, e.g. by providing a combined expression profile, lead to improved prognostic and predictive relevance in cancer diagnostics compared to alternatively considering the CTC expression profile or the EV expression profile alone. The combination of the CTC and EV expression profiles unexpectedly improved diagnostic, prognostic and predictive power as compared to an individual CTC or EV expression profile.

This will be illustrated in the following examples where observed correlations of biomarker expression and therapy response are explained. Correlations were calculated by one-tailed Fisher's exact test and p-values of ≤0.05 were interpreted as significant.

Example 2—Overexpression of at Least One of the Receptor Tyrosine Kinases HER2, HER3, cKIT and cMET in CTCs or EVs Correlates with Therapy Failure Patients and Experimental Workflow The expression profiles of circulating tumor cells (CTCs) and extracellular vesicles (EVs) were generated from a total of 90 blood samples collected from 30 metastatic breast cancer patients at the time of disease progression (T0) and at two consecutive clinical staging time points (T1 and T2) in the course of the therapy (for further details refer to EXAMPLE 1). Patients with stable disease (Responder) and progressive disease (Non-Responder) were identified according to RECIST criteria and further subdivided biomarker positive (pos) and biomarker negative (neg) patients. "Positive" means that overexpression was determined, "negative" means that overexpression was not determined (for calculation see EXAMPLE 1).

Results

Overexpression of four receptor tyrosine kinases (TKs; TK ALL=HER2, HER3, cKIT and cMET) was analyzed in CTCs and EVs. Generally, the four TKs were more frequently overexpressed in CTCs as compared to EVs, wherein in the analysed patients HER2 was exclusively overexpressed in CTCs. No correlation of HER2 to therapy response could be detected in CTCs of the analyzed patients (p=0.10; FIG. 1A). HER3, however, was found to be overexpressed in CTCs and EVs. A significant correlation to therapy response (Non-responder) was observed when analyzing HER3 in CTCs (0.012) which was further increased when combining the results of HER3 signals in CTCs or EVs (0.004). When assessing both, HER2 and HER3 in combination, overexpression of either HER2 or HER3 in CTCs correlated with therapy failure (p=0.005; FIG. 1B). This correlation was even more significant, when analysis was done on all four TKs in CTCs, wherein in 37% of the samples an overexpression of at least one of the four TKs could be detected (p=0.004; FIG. 1C). Surprisingly and in spite of the lower frequency of TK overexpression in EVs, combined analysis of TK expression profiles in CTCs and EVs yielded the most significant results (p=0.001; FIG. 1D).

In addition to increased significance, also the percentage of samples with detectable overexpression of at least one of the four TKs in either CTCs or EVs increased to 49% which not least reflects the increased predictive power of the invention.

It was further observed that the therapy failure correlation was mainly related to chemotherapy (CTX) rather than to denosumab therapy. Patients that did not overexpress any of the four TKs in CTCs responded well to CTX (p=0.0008), whereas patients overexpressing at least one of the four TKs in CTCs did not (p=0.57).

Example 3—Overexpression of AURKA in EVs or CTCs Correlates with Resistance to Denosumab Patients and Experimental Workflow The expression profile of extracellular vesicles (EVs) was generated from a total of 90 blood samples collected from 30 metastatic breast cancer patients at the time of disease progression (T0) and at two consecutive clinical staging time points (T1 and T2) in the course of the therapy (for further details refer to EXAMPLE 1). Patients with stable disease (Responder) and progressive disease (Non-Responder) were identified according to RECIST criteria and further subdivided into patients who did not get Denosumab therapy (w/o Denosu) and patients who were treated with Denosumab (w/Denosu). Denosumab is an anti-RANKL antibody used for the treatment of cancer patients, e.g. to prevent or treat bone metastasis.

Results

Figure 2:
FIGS. 2A and 2B show the relation of AURKA expression to responsiveness to Denosumab therapy in MBC patients (Example 3). The graphs depict the frequency of samples derived from patients who had been treated with Denosumab (w/Denosu) or without Denosumab treatment (w/o Denosu) within the groups of Responders and Non-Responders.

Patients that were found positive for AURKA in EVs showed a correlation with Denosumab treatment failure. This was demonstrated in patients overexpressing AURKA in EVs (AURKA(EV)POS) where no correlation to therapy response could be detected, thereby suggesting a correlation of AURKA overexpression to Denosumab treatment failure (p=0.13; FIG. 2A). In contrast, in the AURKA(EV)NEG group, patients responded very well to the treatment with Denosumab and was correlated to therapy response (p=0.0023; FIG. 2B). Accordingly, patients that did not overexpress AURKA in EVs responded well to denosumab therapy (p=0.0023), whereas patients overexpressing AURKA in EVs did not (p=0.13).

Importantly, combination of patients overexpressing AURKA in CTCs (that were not significant alone) and AURKA(EV)POS patients led to a significant correlation of AURKA overexpression to Denosumab treatment failure (p=0.0024). In addition to increased significance upon combined analysis of expression profiles, also the percentage of samples with detectable overexpression of AURKA increased from 38% (AURKA in EVs only) to 43% (AURKA in CTCs or EVs) which reflects the increased predictive value of the invention.

Example 4—Inverse Correlation of Therapy Response to mTOR Overexpression in CTCs and EVs Patients and Experimental Workflow The expression profiles of circulating tumor cells (CTCs) and extracellular vesicles (EVs) were generated from a total of 90 blood samples collected from 30 metastatic breast cancer patients at the time of disease progression (T0) and at two consecutive clinical staging time points (T1 and T2) in the course of the therapy (for further details refer to EXAMPLE 1). Patients with stable disease (Responder) and progressive disease (Non-Responder) were identified according to RECIST criteria.

Depending on the patients' response at the different time points, four response groups were defined:
Overall Responder: Therapy response at T1 and T2
Overall Non-Responder: No therapy response at T1 and T2
Late Responder: Therapy failure at T1 but response at T2
Late Non-Responder: Therapy response at T1 but failure at T2

Patients of each of the four response groups were further subdivided into patients who did not overexpress mTOR (neg) and patients with mTOR overexpression (pos).

Results

Figure 3:
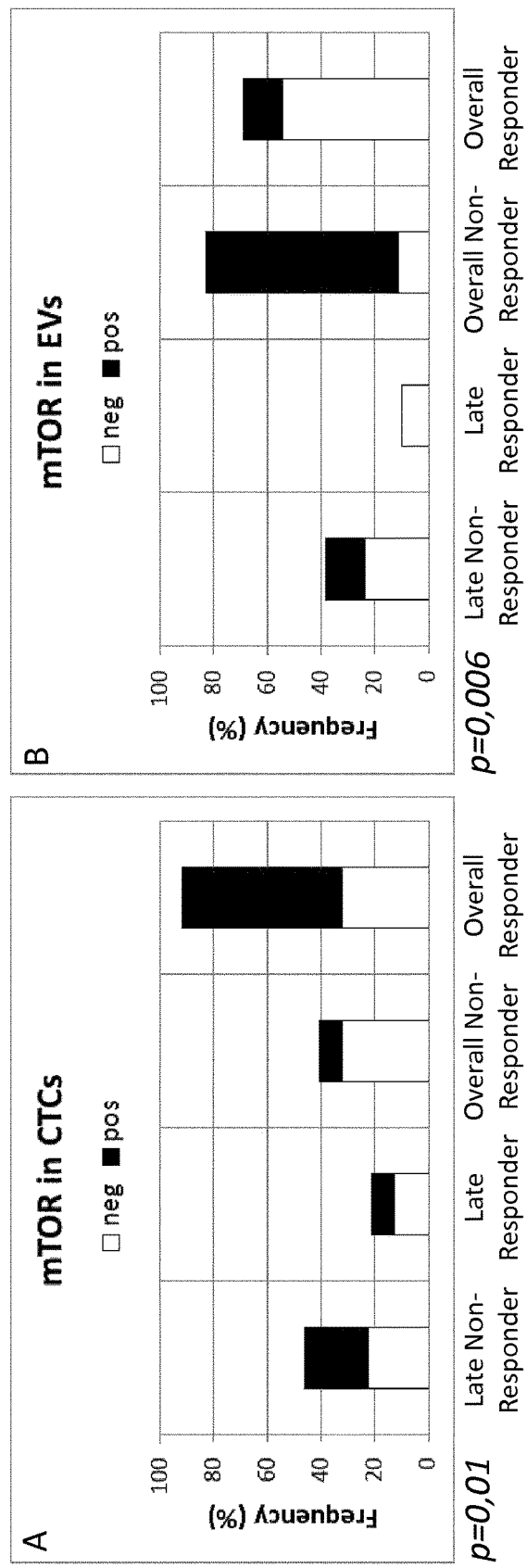
FIGS. 3A and 3B show the relation of mTOR expression to therapy response in MBC patients (Example 4). The graphs depict the frequency of mTOR positive (pos) and mTOR negative (neg) samples within the groups of Overall Responders, Overall Non-Responders, Late Responders and Late Non-Responders.
Figure 4:
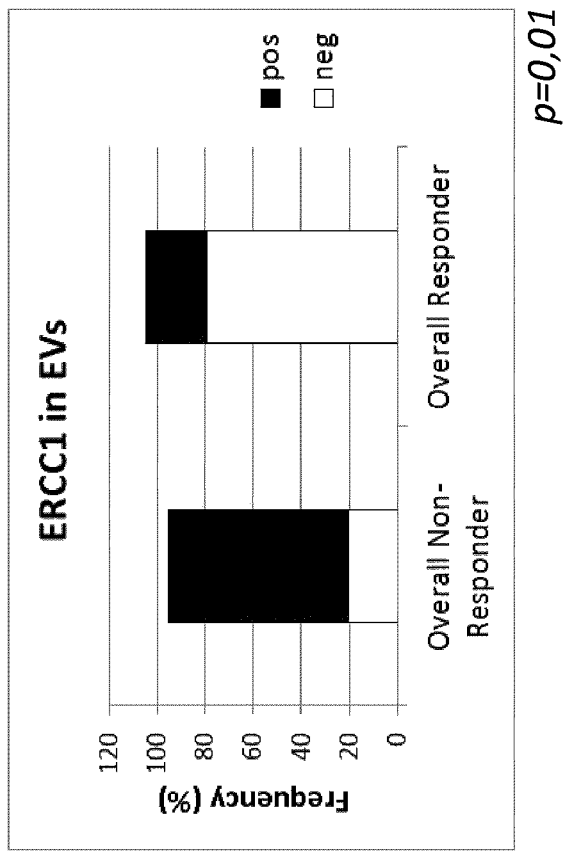
FIG. 4 shows the relation of ERCC1 expression to therapy response in MBC patients (Example 5). The graph depicts the frequency of samples positive (pos) or negative (neg) for ERCC1 in EVs within the groups of Overall Responders and Overall Non-Responders.

Surprisingly, mTOR overexpression in CTCs correlated with better overall response to therapy (p=0.01; FIG. 3A). This is surprising in a way that mTOR is regarded as a key factor in epithelial to mesenchymal transition which is correlated to the PI3K-pathway and, thus, often discussed to represent an indicator for worse outcome.

In more detail, this positive effect of mTOR in CTCs was correlated to chemotherapy (p=0.0065). This was supported by the finding that no correlation to chemotherapy response could be detected anymore for patients without mTOR overexpression in CTCs (p=0.43).

While mTOR overexpressing CTCs were identified in all four response groups, the positive correlation to therapy response was predominantly identified in the overall responder group where approx. 59% had mTOR positive CTC samples, versus approx. 8.5% in overall non-responders; approx. 8.5% in late responders and approx. 24% in late non-responders.

However, contrary to what was found in CTCs, mTOR overexpression in EVs correlated with overall non-responders and thus therapy failure (p=0.006; FIG. 3B). This negative correlation was predominantly identified in the overall non-responder group (approx. 71% of mTOR EV positive samples; versus approx. 14.2% in overall responders; approx. 14% in late non-responders and 0% in late responders).

These data again reflect the increased predictive value of the invention as compared to conventional methods.

EXAMPLES 1-4 demonstrate that the transcriptome analyses of CTCs and the corresponding EVs led to highly differential expression profiles. The examples show that certain biomarkers have a different preference to the analyte type (CTC or EV).

In that context, tyrosine kinases (TKs=HER2, HER3, cKIT and cMET) were found in CTCs with higher incidence and could be correlated with therapy, especially chemotherapy, failure when overexpressed in CTCs (37% of the samples). Combination of TK-profiles derived from CTCs and EVs led to an even more significant correlation with therapy, especially chemotherapy, failure (49%) which clearly affirms the increased overall sensitivity of the inventive method (37% to 49%).

AURKA was predominantly found in EVs and correlated with Denosumab therapy failure (anti-RANKL antibody to protect against bone metastasis). Surprisingly, if combined with patients overexpressing AURKA in CTCs, a positive supplementary effect was given raising overall sensitivity from 38% to 43%.

mTOR was found to be overexpressed in CTCs and EVs. However, depending on the analyte type analyzed (CTCs or EVs), mTOR overexpression inversely correlated with overall response or therapy failure, respectively. While mTOR was predominantly overexpressed in CTCs derived from overall responders, it was mainly correlated with overall therapy resistance when overexpressed in EVs.

These examples clearly reflect the increased predictive value of the invention wherein the CTC expression profile and the EV expression profile is used for a combined analysis of the results, as compared to conventional methods which focus on a single analyte type only (either CTCs or EVs).

Example 5—Overexpression of ERCC1 in EVs Correlates with Therapy Failure

Patients and Experimental Workflow

The expression profile of extracellular vesicles (EVs) was generated from a total of 90 blood samples collected from 30 metastatic breast cancer patients at the time of disease progression (T0) and at two consecutive clinical staging time points (T1 and T2) in the course of the therapy (for further details refer to EXAMPLE 1). Patients with stable disease (Responder) and progressive disease (Non-Responder) were identified according to RECIST criteria. Depending on the patients' response at the different time points, four response groups were defined:
Overall Responder: Therapy response at T1 and T2
Overall Non-Responder: No therapy response at T1 and T2
Late Responder: Therapy failure at T1 but response at T2
Late Non-Responder: Therapy response at T1 but failure at T2

Patients of each of the four response groups were further subdivided into patients who did not overexpress ERCC1 (neg) and patients with ERCC1 overexpression (pos).

Results

ERCC1 overexpression in EVs correlated with overall non-responders and thus therapy failure (p=0.01). The portion of ERCC1 overrepresentation in EVs increases with increasing therapy resistance, suggesting ERCC1 in EVs as negative response marker.

The invention claimed is:
1. A method for determining the effectiveness of an anti-RANKL antibody therapy being administered to a subject afflicted with cancer, the method comprising steps:
(A) isolating RNA from circulating tumor cells obtained from the subject, determining expression of at least AURKA in the RNA isolated from the circulating tumor cells, and generating an expression profile for the circulating tumor cells that includes the determined expression of AURKA in the RNA isolated from the circulating tumor cells;
(B) isolating RNA from extracellular vesicles obtained from the subject, determining expression of at least AURKA in the RNA isolated from the extracellular vesicles, and generating an expression profile for the extracellular vesicles that includes the determined expression of AURKA in the RNA isolated from the extracellular vesicles;
(C) generating a combined expression profile that comprises the determined expression of AURKA for the circulating tumor cells from step (A) and the determined expression of AURKA for the extracellular vesicles from step (B);
(D) identifying whether AURKA is overexpressed in the combined expression profile generated in step (C), wherein overexpressed means that AURKA is expressed in the combined expression profile of the subject above a threshold value predetermined on the basis of normalized AURKA expression data from a plurality of subjects not afflicted with cancer; and

(E) when AURKA is identified in the combined expression profile as being overexpressed in step (D), ceasing the administration of the anti-RANKL antibody therapy previously being administered to the subject and instead administering a therapeutic agent that is different than the anti-RANKL antibody therapy previously administered to the subject to treat the cancer.

2. The method according to claim 1, wherein the method comprises a), b) or c), where:
   a) is
      providing a liquid biological sample obtained from the subject;
      removing cells from the liquid biological sample, thereby providing a cell-depleted biological sample;
      isolating circulating tumor cells from the removed cells;
      wherein step (A) comprises isolating RNA from the isolated circulating tumor cells; and
      wherein step (B) comprises isolating RNA from extracellular vesicles comprised in the cell-depleted biological sample;
   b) is:
      providing a liquid biological sample obtained from the subject;
      isolating circulating tumor cells from the liquid biological sample;
      removing remaining cells from the liquid biological sample from which the circulating tumor cells were isolated thereby providing a cell-depleted biological sample;
      wherein step (A) comprises isolating RNA from the isolated circulating tumor cells; and
      wherein step (B) comprises isolating RNA from extracellular vesicles comprised in the cell-depleted biological sample; and
   c) is:
      providing at least two liquid biological samples of the same kind obtained from the same subject;
      isolating circulating tumor cells from at least one of the liquid biological samples, wherein step (A) comprises isolating RNA from the isolated circulating tumor cells; and
      obtaining a cell-depleted sample from at least one of the liquid biological samples, wherein step (B) comprises isolating RNA from extracellular vesicles comprised in the cell-depleted biological sample.

3. The method according to claim 1, wherein determining the expression of AURKA in the isolated RNA in either or both of step (A) and step (B) comprises any one or more of the following:
   (i) it comprises reverse transcription to obtain cDNA; and
   (ii) it comprises performing a quantitative polymerase chain reaction.

4. The method according to claim 1, wherein the biological sample has any one or more of the following characteristics:
   it is a liquid biopsy sample:
   it is a bodily fluid;
   it is selected from blood, urine, peritoneal effusions and pleural effusions, bone marrow aspirates and nipple aspirates;
   it is selected from blood and urine; and
   it is blood.

5. The method according to claim 1, wherein determining the expression of AURKA in the isolated RNA in either or both of step (A) and step (B) comprises:
   (i) reverse transcription to obtain cDNA; and
   (ii) at least one step of amplifying the cDNA.

6. The method according to claim 5, wherein determining the expression of AURKA in the isolated RNA in either or both of step (A) and step (B) further comprises performing a quantitative polymerase chain reaction.

7. The method according to claim 1, wherein the anti-RANKL antibody is denosumab.

8. The method according to claim 7, wherein the threshold value is predetermined to achieve a specificity of at least 90% for AURKA.

9. The method according to claim 7, wherein the denosumab is being administered to the subject as denosumab bone stabilization therapy, and wherein overexpression of AURKA indicates denosumab bone stabilization therapy failure or resistance to denosumab bone stabilization therapy.

* * * * *